US010383955B2

(12) United States Patent
Arock et al.

(10) Patent No.: US 10,383,955 B2
(45) Date of Patent: Aug. 20, 2019

(54) HUMAN MAST CELL LINES, PREPARATION AND USES

(71) Applicants: CENTRE NATIONAL DE LA RECHERCHE SCIENTIFIQUE, Paris (FR); ECOLE NORMALE SUPERIEURE DE CACHAN, Cachan (FR); MEDIZINISCHE UNIVERSITÄT WIEN, Vienna (AT)

(72) Inventors: Michel Arock, Paris (FR); Peter Valent, Vienna (AT); Rosine Saleh, Asnieres sur Seine (FR); Ghaith Wedeh, Antony (FR); Christian Auclair, Paris (FR)

(73) Assignees: CENTRE NATIONAL DE LA RECHERCHE SCIENTIFIQUE, Paris (FR); ECOLE NORMALE SUPERIEURE DE CACHAN, Cachan (FR); MEDIZINISCHE UNIVERSITAT WIEN, Vienna (AT)

( * ) Notice: Subject to any disclaimer, the term of this patent is extended or adjusted under 35 U.S.C. 154(b) by 694 days.

(21) Appl. No.: 14/355,938

(22) PCT Filed: Nov. 2, 2012

(86) PCT No.: PCT/EP2012/071731
§ 371 (c)(1),
(2) Date: May 2, 2014

(87) PCT Pub. No.: WO2013/064639
PCT Pub. Date: May 10, 2013

(65) Prior Publication Data
US 2014/0298497 A1    Oct. 2, 2014

(30) Foreign Application Priority Data

Nov. 2, 2011 (FR) ..................... 11 59902

(51) Int. Cl.
*A61K 49/00* (2006.01)
*C12N 5/0787* (2010.01)
*G01N 33/50* (2006.01)

(52) U.S. Cl.
CPC ........ *A61K 49/0008* (2013.01); *C12N 5/0642* (2013.01); *G01N 33/5008* (2013.01); *G01N 33/5047* (2013.01)

(58) Field of Classification Search
None
See application file for complete search history.

(56) References Cited

U.S. PATENT DOCUMENTS

2012/0093781 A1* 4/2012 Mohapatra ........... C12N 5/0642
424/93.7

FOREIGN PATENT DOCUMENTS

| WO | WO 03/065986 | 8/2003 |
| WO | WO 2003065986 | * 8/2003 |
| WO | WO 2010/105215 | 9/2010 |

OTHER PUBLICATIONS

Kaur et al., Allergy, 2006, v.61, pp. 1047-1053.*
Anderson et al., J of Immunol, 2008, v.336, pp. 166-174.*
Escribano et al., Internat.Archives of Allergy and Immunol., 2002, v.127, pp. 127-132).*
Glaum et al., ( J of Allergy and Clinical Immunology, 2009, v.123, N:2, p. S197.*
Laidlaw, T. M. et al. "Characterization of a novel human mast cell line that responds to stem cell factor and expresses functional FcεRI" *Journal of Allergy and Clinical Immunology*, Mar. 2011, pp. 815-822.e-5, vol. 127, No. 3.
Guhl, S. et al. "Mast cell lines HMC-1 and LAD2 in comparison with mature human skin mast cells—drastically reduced levels of tryptase and chymase in mast cell lines" *Experimental Dermatology*, Sep. 2010, pp. 845-847, vol. 19, No. 9.
Gibbs, B. F. et al. "Effects of Stem Cell Factor on Hypoxia-Inducible Factor 1 Alpha Accumulation in Human Acute Myeloid Leukaemia and LAD2 Mast Cells" PLOS ONE, Jul. 2011, pp. 1-10, vol. 6, No. 7.
Molfetta, R. et al. "Negative signals from FcεRI engagement attenuate mast cell functions" *Archivum Immunologiae et Therapiae Experimentalis*, Aug. 2007, pp. 219-229, vol. 55, No. 4.
Written Opinion in International Application No. PCT/EP2012/071731, dated Feb. 15, 2013, pp. 1-9.

* cited by examiner

*Primary Examiner* — Michail A Belyavskyi
(74) *Attorney, Agent, or Firm* — Saliwanchik, Lloyd & Eisenschenk

(57) ABSTRACT

The present invention relates to a human mast cell line corresponding to deposit number CNCM I-4551 and also to the lines derived therefrom, in particular the derived lines corresponding respectively to deposit numbers CNCM I-4552 and CNCM I-4553, and to the uses thereof, in particular for screening for compounds of therapeutic interest.

Figure 1:
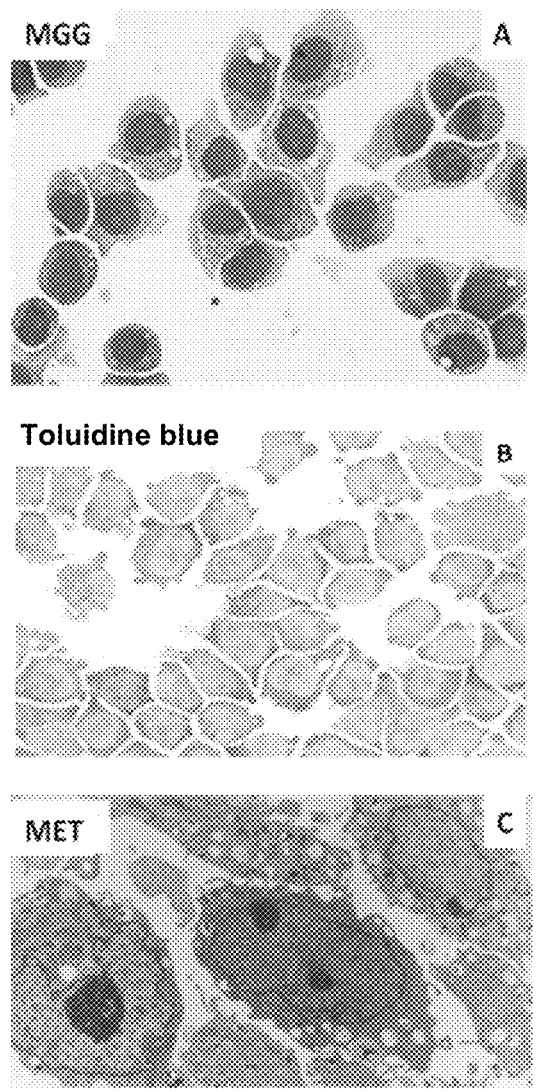

5 Claims, 19 Drawing Sheets
Specification includes a Sequence Listing.

ROSA KIT Del417-419insY

ROSA KIT D816V

HUMAN MAST CELL LINES, PREPARATION AND USES

CROSS-REFERENCE TO RELATED APPLICATION

This application is the U.S. national stage application of International Patent Application No. PCT/EP2012/071731, filed Nov. 2, 2012.

The Sequence Listing for this application is labeled "Seq-List.txt" which was created on May 1, 2014 and is 39 KB. The entire contents of the sequence listing is incorporated herein by reference in its entirety.

The present invention relates to a novel human mast cell line (identified in the present text as ROSA KIT WT line), the cells of which express the wild-type KIT receptor (also identified as CD117, KIT wild-type or WT KIT in the present text) and also the high-affinity IgE receptor (also identified as FcεR1 or FcepsilonR1 receptor in the present text), and also to any derived cell line, any derived cell clone and any mutant of said human mast cell line which has retained at least one of said morphological, ultrastructural, phenotypic and/or functional characteristics of said ROSA KIT WT line. This line has been obtained from cells originating from the umbilical cord blood of a healthy human subject. The invention also relates to particular lines of cells derived from the ROSA KIT WT line, in particular the lines identified in the present text as "ROSA KIT D816V" and "ROSA KIT Delta 417-419 insY" which have a mutated KIT receptor (CD117).

The invention also relates to the use of the described lines in research, in diagnosis and/or in therapy, in particular for screening for molecules of interest in the treatment of pathological conditions in which mast cells are involved (allergies, inflammatory diseases, cancers), in particular in which mast cells have a deleterious role.

PRIOR ART

Allergy is one of the most common pathological conditions (15-20%) and constitutes, whatever its form, a health problem which is worrying since it is constantly on the increase in industrialized countries. In most cases, allergy is linked to a deviation in the normal immune response resulting in the synthesis of particular immunoglobulins, of E type (IgE), directed against environmental antigens (pollens, dust bites, pet hairs and dander, food antigens, etc.). The IgE-dependent effector cells of the allergic reaction are the mast cells (MCs). Mast cells are cells with a ubiquitous tissue distribution, derived from CD34+ (nonengaged) multipotent haematopoietic cells, which play an important role in the initiation of the innate and adaptive immune response, and also in IgE-dependent allergic reactions and in various inflammatory reactions. Indeed, mast cells express, at their surface, a large number of high-affinity receptors for immunoglobulin E (FcepsilonR1 or FcεR1). These receptors bind the Fc fragment of these immunoglobulins, thereby stabilizing them at the surface of the cell for months or even years. During a contact with the allergen corresponding to these IgEs, there is an aggregation of the receptors by the allergen, resulting in the activation of a signalling cascade ("signal transduction") inside the cells. This activation is followed, in a few seconds, by massive degradation of the cells with the release of preformed mediators, for instance histamine, heparin and proteases such as tryptase. A few minutes later, the activated cell synthesizes, de novo, large amounts of arachidonic acid derivatives (leukotrienes and prostaglandins) from the membrane lipids. These preformed and neosynthesized mediators released earlier by the activated mast cell play a central role in the immediate allergic reaction which can range from simple allergic rhinitis to anaphylactic shock which is sometimes lethal. In addition, a few hours after the IgE-dependent activation, the mast cell synthesizes and releases myriad cytokines and chimiokines which intervene in the delayed phase of the allergic reaction by attracting and activating other cell types (eosinophil and neutrophil polymorphonucleocytes, lymphocytes, monocytes) which thus participate in the chronic destruction of tissues, as is the case, for example, during allergic asthma.

At the current time, there is no easily administrable and systematically acting therapeutic which targets the molecular mechanisms of IgE-dependent activation. Indeed, most "anti-allergic" therapeutics currently used are purely symptomatic and aim to inhibit the deleterious effects of the mast-cell mediators released during the activation of these cells (antihistamines, anti-leukotriens, etc.).

In order to be able to study the molecular mechanisms linked to the IgE-dependent activation of mast cells and to develop methods of screening for molecules capable of specifically inhibiting this activation, it is necessary to be able to have pure populations of functional human mast cells, ideally in large amounts. One of the possibilities consists of purifying human mast cells from tissues. Although this is theoretically possible, in practice the yield from these techniques is low (a maximum of 1 to 3 million mast cells) and the methods used, in addition to being expensive, are detrimental to obtaining functional mast cells.

In order to bypass this difficulty, the inventors have developed a technique for culturing in liquid medium in the continuous presence of Stem Cell Factor (SCF) in order to obtain pure populations of normal human mast cells starting from umbilical cord blood CD34+ stem cells. These CD34+ cells are first purified by immunoaffinity and placed in culture in a liquid medium in the presence of SCF which promotes their differentiation into mast cells. After 8 to 10 weeks of culturing under these conditions, they obtain pure populations (more than approximately 99%) of mast cells which no longer proliferate and which cannot be frozen.

These cells are then used in IgE-dependent activation tests.

However, this type of primary culture has the major drawbacks identified below:
  it is necessary to repeatedly place in culture CD34+ cells originating from different umbilical cord bloods so as to be able to have sufficient amounts of mast cells throughout the experiments, this additionally being very expensive because of the reagents used for the purification of the CD34+ cells;
  the yield in terms of obtaining mast cells at the end of culturing is extremely variable from one umbilical cord blood to another and never exceeds 200 million cells in the end; and
  the morphological and functional characteristics of the mast cells obtained at the end of culturing vary from one umbilical cord blood to the other. The experiments therefore need to be repeated with several batches of mast cells in order to obtain statistically significant results.

In addition to their role during allergic and/or inflammatory reactions, human mast cells are, moreover, implicated in a group of rare tumour pathologies: mastocytoses.

Mastocytoses constitute a heterogeneous group of conditions characterized by the accumulation or abnormal proliferation of mast cells in various organs or tissues. They are rare and are described as "orphan diseases" (incidence of 200,000-300,000 patients/year), they most commonly occur sporadically but are sometimes familial, and they are especially very heterogeneous with regard to their clinical expression, the ways in which they progress and their prognosis. The physiopathology of these diseases remains poorly understood and treatments are not very specific. The skin is the only tissue involved in cutaneous mastocytoses, which are benign conditions observed preferentially in children, and which often resolve spontaneously. Systematic mastocytoses are defined by the involvement of one or more viscera or tissues, generally the bone marrow, with or without cutaneous involvement. They represent 10% to 30% of mastocytoses, generally occur in adults (average age at diagnosis: 60 years old) without sex predilection, and are relatively frequently associated with a myeloid haemophathy.

The study of the physiopathological mechanism of mastocytoses was first directed towards the search for synthesis abnormalities relating to the KIT ligand, Stem Cell Factor (SCF). The conclusions of these studies made it possible to discard this hypothesis. The teams then focused directly on the KIT receptor. This is because the activation of KIT was noted in the absence of the SCF ligand in mast cell lines (HMC-1 line). Cases of KIT-activating mutations were also observed in myeloid haemopathies.

The KIT receptor is a single-stranded transmembrane receptor which belongs to the family of receptors with intrinsic tyrosine kinase activity. It comprises, at the intracytoplasmic level, a kinase domain 1, which is an ATP binding site, and a kinase domain 2, which is a phosphotransferase activity site. It is expressed by various cell types: mast cells, haematopoietic progeniters, melanocytes, germinal cells and interstitial cells of Cajal. Activation of the KIT receptor causes dimerization and phosphorylation thereof. The phosphorylated tyrosines act as binding sites for molecules which relay signal transduction. Thus, various signalling pathways are activated and generate cell proliferation, survival or activation signals according to the receptivity of the cell.

With regard to the structure of KIT during mastocytoses, the results of these studies have shown the following facts:

In adult patients suffering from indolent systematic mastocytosis, more than 85% of cases show the same acquired KIT-activating mutation, affecting the amino acid occupying position 816 of the amino acid sequence SEQ ID NO: 2 of the wild-type KIT receptor (VVT KIT) (mutation Asp816Val or mutation D816V resulting in the substitution of the asparagine occupying position 816 of SEQ ID NO: 2 by valine—see SEQ ID NO: 4 corresponding to the amino acid sequence of the KIT D816V mutant receptor), located in the phosphotransferase domain (corresponding to the amino acids occupying positions 762 to 937 of SEQ ID NO: 2). The other adult patients exhibit either a normal structure of the WT KIT receptor (corresponding to SEQ ID NO: 2), or rare abnormalities or mutations (deletions, insertions, etc.) which may be located either in the phosphotransferase domain or in the juxtamembrane domain of the KIT receptor (corresponding to the amino acids occupying positions 543 to 582 of SEQ ID NO: 2). Most of these abnormalities, and in particular KIT D816V, are transforming abnormalities both in vitro on cell lines and in vivo in mice.

In children, the situation is different. While more than 80% of children exhibit a KIT abnormality (the remainder exhibiting a WT KIT), the KIT D816V mutation is not predominant in these patients. Specifically, 36% of children exhibit this mutation, while 44% of children exhibit particular mutations (of types such as deletion, substitution, duplication or insertion of one or more nucleotides) of exon 8 (corresponding to the nucleotides occupying the positions 1237 to 1352 of the nucleotide sequence SEQ ID NO: 1 encoding the WT KIT receptor) or of exon 9 (corresponding to the nucleotides occupying positions 1353 to 1547 of the nucleotide sequence SEQ ID NO: 1 encoding the WT KIT receptor of sequence SEQ ID NO: 2), together forming the "Ig5-like" domain, which encode the extramembrane part of the receptor (corresponding to the amino acids occupying positions 26 to 519 of SEQ ID NO: 2), several of these particular mutations having been described in other types of malignant pathological conditions, such as acute myeloid leukaemias or gastrointestinal stromal tumours. The KIT Delta417-419 insY, KIT S4761, KIT ITD502-503 and KIT K5091 mutations are examples of such abnormalities capable of affecting the sequence SEQ ID NO: 2 of the wild-type KIT receptor. Here again, these abnormalities are transforming in vitro and in vivo.

At the current time, the treatment for mastocytoses, in particular in adults, is disappointing. Indeed, while imatinib has shown a certain efficacy in patients exhibiting a WT KIT or KIT abnormalities at the juxtamembrane level, this molecule is completely inactive on the KIT D816V mutation, the one most commonly encountered in adults. In addition, although dasatinib, another tyrosine kinase inhibitor, has an advantageous activity in vitro on the D816V mutation, its progression into therapy has proved to be disappointing because of a lower efficacy than anticipated and high toxicity in humans. Treatment of the aggressive forms with the KIT D816V mutation thus currently calls upon chemotherapies which are relatively nonspecific and extensive, and not without side effects.

It thus becomes necessary to have cell models of human mast cells which can be easily manipulated, which have the KIT-activating mutation D816V, and which make it possible to perform screening tests, in particular high-throughput screening tests, in order to search for and identify molecules capable of specifically and therefore more effectively targeting this KIT abnormality.

The human mast cell lines currently available are the following:

1) The HMC-1 line derived from the peripheral blood of a patient suffering from mastocytosis. In addition to the fact that it is a leukaemia line which has numerous other molecular abnormalities that may be involved in the abnormal proliferation of these cells (not found in patients suffering from systematic mastocytosis), this line has major limitations:

it absolutely does not express the FcepsilonR1 receptor and thus cannot be activated by this means (cf. Guhl et al., "*Mast cell lines HMC-1 and LAD2 in comparison with mature skin mast cells drastically reduced levels of tryptase and chymase in mast cell lines*", Vol. 19, No. 9, September 2010, pages 845-847), it does not comprise a clone carrying only the KIT D816V mutation (the mutation responsible for the spontaneous tyrosine kinase activity of the KIT receptor, encountered in more than 85% of patients suffering from systemic mastocytosis), and it does not comprise a clone expressing only the wild-type KIT receptor (VVT KIT). This model can be used neither for screening for molecules with potential anti-allergic activity, nor for studying the interactions between the signalling induced by KIT activation and the signalling induced by FcepsilonR1 (FcεR1) activation during mastocytoses, nor for measuring any non-specific KIT D816V toxicity of any molecule potentially targeting this abnormality.

2) The LAD-2 line and its subclones (cf. WO 2003/065986 and Gibbs Bernhard et al., "*Effects of Stem Cell Factor on Hypoxia-Inducible Factor* 1 *Alpha Accumulation in Human Acute Myeloid Leukaemia and LAD2 Mast Cells*", Vol. 6, No. 7, July 2011): it is a mast cell line derived from the bone marrow of a patient suffering from a mast cell sarcoma (systematic mastocytosis) and which expresses the high-affinity IgE receptor and the WT KIT receptor. This line, which remains SCF-dependent for its survival and its proliferation, is potentially advantageous but, in addition to the fact that it was obtained from a tumour sample, its very long doubling time of about 15 days makes it unsuitable for use in high-throughput screening tests which require the simultaneous obtaining of a large number of cells.

3) The LUVA line: it is a line derived from the peripheral blood cells of an allergic patient. It is independent of any growth factor for its proliferation and exhibits the high-affinity IgE receptor. It is therefore potentially advantageous, but again, it is a line obtained from a sample taken from a non-healthy patient. In addition, its long doubling time also makes it unsuitable for use in the context of high-throughput in vitro screening. Finally, this line does not make it possible to study the signalling via the WT KIT receptor and does not enable high-throughput screening for molecules which specifically inhibit this receptor.

4) The USF-MC1 line (WO 2010/105215): it is an SCF-independent line derived from umbilical cord blood progenitors, which exhibits the high-affinity IgE receptor, but has been transformed by the SV40 virus. It is therefore impossible to anticipate the effects of this transformation on the signalling of the high-affinity IgE receptor. This line does not make it possible to study the signalling by the WT KIT receptor and does not enable high-throughput screening for molecules which specifically inhibit this receptor.

The only cell model of human mast cells, bearing a KIT mutation, available at the current time is the HMC-1 line and its two subclones HMC-1.1 and HMC-1.2. Indeed, HMC-1, like the subclone HMC-1.1, exhibits a juxtamembrane KIT V560G mutation and is sensitive to imatinib, while the subclone HMC-1.2 exhibits two KIT mutations (V560G and D816V) and is sensitive to dasatinib but not to imatinib. The major drawbacks of these lines are the following:

1) there is no clone which carries only the D816V mutation, making it possible to interpret any selective effect of a molecule on the isolated D816V mutation;
2) there is no clone which expresses only WT KIT, making it possible to measure any nonspecific KIT D816V toxicity of a molecule potentially targeting this abnormality;
3) the HMC-1 line is a leukaemia line exhibiting numerous molecular abnormalities other than the mutated KIT, which may be involved in the abnormal proliferation of these cells, and not found in patients suffering from systematic mastocytosis; and
4) these lines do not express the high-affinity IgE receptor and therefore prohibit any analysis of the possible interactions between the KIT signalling pathways and those of FcepsilonR1.

Thus, at the current time, the cell models that can be used in the context of the allergies or malignant pathological conditions mentioned above have numerous limitations, either because they are not very reproducible and expensive to produce (primary culture models), or because they are distant from the mast cell in terms of biological properties.

SUMMARY OF THE INVENTION

The inventors presently describe, for the first time, a line of human mast cells expressing the wild-type KIT receptor and also the high-affinity IgE receptor (FcεR1), which can be activated by both or either one and/or another of these receptors, which have a fast doubling time (of at most 72 hours), i.e., compatible with mass production (in view of high-throughput screening tests), which can be easily frozen and thawed, and the morphological, ultrastructural, phenotypic and functional characteristics of which remain stable over time. The cells of this line, which are obtained from haematopoietic progenitors originating from the umibilical cord blood of a healthy human subject, exhibit characteristics which are the closest known to date to the characteristics of normal human mast cells.

A particular subject of the present invention thus relates to a human mast cell line which has the following morphological, ultrastructural and phenotypic characteristics: i) presence of metachromatic intracytoplasmic granulations, and ii) expression of FcεR1 and wild-type KIT (CD117) receptors, and of CD33, CD203c and CD300a markers.

Another particular subject of the present invention relates to a human mast cell line which has the following functional characteristics: i) strict dependence with respect to SCF for its survival and its growth, ii) doubling time of at most 72 hours, typically of 48 hours, iii) FcεR1 expression increased by treatment with interleukin 4 (IL-4) and/or with human IgEs, iv) CD117 expression decreased by treatment with interleukin 4 (IL-4), and v) immediate increase in membrane expression of CD203c and/or immediate release of histamine, of beta-hexosaminidase and of tryptase, and delayed release of TNF-α, by activation:
  i) in the presence of specific IgE and of the antigen capable of binding to said specific IgE,
  ii) in the presence of IgE and of anti-IgE, or
  iii) in the presence of anti-FcεR1 receptor antibody.

A preferred subject of the invention is a human mast cell line which has all of the morphological, ultrastructural, phenotypic and functional characteristics identified above.

The invention also relates to any derived cell line, cell clone or mutant of a human mast cell line according to the invention having retained at least one, preferably several, and ideally all of the morphological, ultrastructural, phenotypic and/or functional characteristics identified above.

A human mast cell line which is preferred according to the invention is the human mast cell line identified as ROSA KIT WT as registered under deposit number CNCM 1-4551 with the CNCM [French National Collection of Microorganism Cultures] on 2 Nov. 2011.

The inventors also describe cell clones derived from the ROSA line which exhibit respectively the KIT activating mutations most commonly encountered in mast cells (KIT D816V and KIT Delta 417-419 insY), and also preferred mast cell lines, derived from the ROSA KIT WT human mast cell line, said derived lines being respectively identified as ROSA KIT D816V (as registered under deposit number CNCM 1-4552 with the CNCM on 2 Nov. 2011) and ROSA KIT Delta 417-419 insY (as registered under deposit number CNCM 1-4553 with the CNCM on 2 Nov. 2011).

Also considered to be subjects of the present invention are the derived mast cell lines, and also the cell clones and the mutants (natural or artificially obtained), of said ROSA KIT WT, ROSA KIT D816V and Delta 417-419 insY lines, having retained at least one of their characteristics.

The invention also relates to a method for preparing a population of human mast cells capable of proliferating for a period greater than 6 months, at least 99% of the cells of which have the characteristics of the cells of a human mast cell line according to the invention of ROSA KIT WT type, and also any population of human mast cells, human mast cell clone or human mast cell line capable of being obtained at the end of such a method. This method comprises culturing haematopoietic precursors originating from the umbilical cord blood of a healthy human subject in a medium comprising at least 25 ng/ml, preferably at least 50 ng/ml, of human Stem Cell Factor (SCF), and obtaining a population of human mast cells having the desired characteristics.

The invention also relates to a method for preparing a mast cell line exhibiting a mutation of the KIT receptor, preferably a KIT receptor activating mutation (responsible for the constitutive activation of the KIT receptor) associated with a pathological condition chosen from mastocytosis, acute leukaemia, lymphoma and a solid tumour, comprising the transformation of a human mast cell line according to the invention, typically a cell line of ROSA KIT WT type, by introduction, into the cells of said line, of a nucleic acid encoding a mutated KIT receptor, so as to obtain a mast cell line exhibiting said KIT mutation.

One particular subject of the invention thus relates to a mast cell line capable of being obtained at the end of the method described above. Such a line exhibits a KIT receptor mutation. Advantageously, this mutation may be responsible i) for the acquisition, by the line, of independence with respect to SCF for its survival and its growth; ii) for the acquisition, by the line, of in vivo tumorigenicity in mammals; iii) for an increase in the capacity of the line to release a mediator of inflammation or of allergy in the presence of specific IgE and of the antigen capable of binding to said specific IgE, in the presence of IgE and of anti-IgE, or in the presence of anti-FcεR1 receptor antibody, or by activation of a receptor of TLR type, of a complement fraction receptor, or of a cytokine or chemokine receptor; iv) for a change, typically an activation, of the intra-mast cell signalling in the line; and/or v) for an interaction of said mutated KIT receptor or of at least one of its signalling pathways with at least one other mast cell receptor or at least one of its signalling pathways.

The invention also relates to any derived cell line, cell clone or mutant of such a human mast cell line according to the invention exhibiting a mutation of the KIT receptor, having retained at least one, preferably several, and ideally all of its morphological, ultrastructural, phenotypic and/or functional characteristics, preferably its functional characteristics.

Other particular subjects of the invention are the cells, cell clones, cell populations and cell subpopulations originating from a mast cell line according to the invention as described in the present text, and also the compositions comprising such subjects.

The invention also relates to a kit (set of tools) for screening for an agent of interest, comprising: i) at least one product chosen from a mast cell line, a cell, a cell clone, a cell population, a cell subpopulation or a composition according to the invention, and preferably ii) written instructions a) explaining the various steps of the culturing and/or of the preserving of the cells, b) detailing the composition of the culture medium or media and/or of the preserving medium for these cells and/or listing one or more growth factors which may be used in the context of the culturing and/or of the preserving of said cells, and/or c) detailing the possible uses of said lines, cells, cell clones, cell populations, cell subpopulations and compositions; and also, optionally, iii) a supplementary product chosen from one or more culture media, one or more maintenance media, one or more growth factors enabling or promoting the culturing of mast cells, and any combination of said products.

The invention relates, moreover, to a non-human animal model comprising at least one cell originating from a mast cell line according to the invention, preferably from a line chosen from the ROSA KIT D816V line, the ROSA KIT Delta 417-419 insY line and a line of ROSA KIT D816V or ROSA KIT Delta 417-419 insY type. It also relates to the use of such a line for evaluating, in vivo, the interest, in particular the preventive or therapeutic interest, of a candidate molecule.

The cell lines according to the invention represent progress in economic terms since they are easy to manipulate and to amplify at a lower cost.

These cell lines can be used as cell models, in particular for screening for molecules which specifically target the high-affinity IgE receptor, the siganlling pathway induced by activation of the high-affinity IgE receptor, the (normal or mutated) KIT receptor, the cell signalling pathway induced by activation of the normal KIT receptor or an abnormal cell signalling pathway induced by activation of a mutated KIT receptor (for example, KIT D816V and KIT Delta 417-419 insY).

These lines can be used to screen for an agent of interest, typically an agent that is of use in the prevention, diagnosis, treatment and/or follow-up of a pathological condition, typically of a pathological condition in which the mast cells play a role, for example a deleterious role.

The pathological condition targeted is preferably chosen from an allergy disease (for example allergic asthma); an inflammatory disease; an autoimmune disease; an infectious disease; non-allergic asthma; urticaria; or a tumour, typically mastocytosis, acute leukaemia, lymphoma or a solid tumour.

DETAILED DESCRIPTION OF THE INVENTION

The invention relates to human mast cell lines optionally having a KIT receptor of normal structure and an FcεR1 receptor, and also to the method for obtaining the same and to the uses thereof.

The invention also relates to the cells, cell clones (also identified in the present text by the term "clone"), cell populations or cell subpopulations originating from the mast cell lines described in the present text, and also to any derived cell line obtained from such a cell, population, subpopulation, or cell clone. The invention also relates to any mutant of a cell line described in the present text which retains at least one characteristic of said line, preferably several, and typically all the characteristics of said line. Such a mutation may be generated spontaneously (natural or spontaneous mutation) or may be intentionally created by human beings by genetic manipulation (artificial mutation).

Moreover, the invention relates to a composition comprising a cell, a cell clone, a cell population (for example a line) and/or a cell subpopulation as described in the present text. It may, for example, be a cell culture, typically a culture of human mast cells, preferably of mast cells having the morphological, ultrastructural, phenotypic and/or functional characteristics described in the present text.

The term "culture" denotes herein, generally, a cell and also a population of cells (the set of cells) grown in vitro.

A culture developed directly from a cell or tissue sample is called a "primary culture" and generally comprises a heterogeneous population of cells.

The term "line" denotes a homogeneous population of cells obtained after at least one step of subculturing a primary culture (step also identified by the term "passage" which makes it possible to obtain a large number of cells from pre-existing cells), typically after several consecutive steps of subculturing (or consecutive passages) of cells originating from a cell population derived from a primary culture.

The term "clone" or "cell clone" denotes a set of cells derived from a single cell, from a primary culture or from a line (Schaeffer, *In Vitro Cellular and Developmental Biology*, 26, 91-101, 1990), for example obtained by the cell line limiting dilution technique.

The invention also relates to a kit (set of tools) for in vitro screening for an agent of interest, comprising: i) at least one product chosen from a mast cell line, a cell, a cell clone, a cell population, a cell subpopulation or a composition according to the invention, and preferably ii) written instructions a) explaining the various steps of the culturing and/or of the preserving of these cells, b) detailing the composition of the culture medium or media and/or of the preserving medium for these cells and/or listing one or more growth factors which may be used in the context of the culturing and/or of the preserving of said cells, and/or c) detailing the possible uses of said lines, cells, cell clones, cell populations, cell subpopulations and compositions; and also, optionally, iii) a supplementary product chosen from one or more culture media, one or more maintenance media, one or more growth factors enabling or promoting the culturing of mast cells, and any combination of said products.

An example of a culture medium which can be provided in the kit is Iscove's modified Dulbecco's Medium (IMDM)-Glutamax® (Invitrogen) supplemented with the following products: penicillin/streptomycin 100 U/ml (P/S) (Invitrogen), 1% of sodium pyruvate (Invitrogen), 1% of vitamins (Invitrogen), 1% of glutamine (Invitrogen), 2% of nonessential amino acids (Invitrogen), 1% of a commercial solution of insulin-transferrin-sodium selenite (Invitrogen) and 0.3% of albumin bovine (BSA) (PAA).

A typical preserving medium comprises 90% of foetal calf serum and 10% of dimethyl sulfoxide (DMSO).

Growth factors which may be used in the context of the culturing and/or of the preserving of the cells according to the invention are, for example, SCF and/or IL-4.

A preferred kit according to the invention, which can be used in the high-throughput tests for screening for molecules which can inhibit the activation of the high-affinity IgE receptor, comprises for example: a) at least one product chosen from the ROSA KIT WT mast cell line, one product derived from said line, chosen from a cell, a cell clone, a cell population, or a cell subpopulation, or a composition according to the invention comprising a product chosen from said line, said cell, said clone, said population and/or said subpopulation, and preferably: b) written instructions explaining the various steps of the culturing and/or of the preserving of said cells, detailing the composition of the culture medium or media and/or of the preserving medium for said cells and/or listing one or more growth factors which may be used in the context of the culturing and/or of the preserving of said cells, c) written instructions describing the various steps, and/or identifying reagents, for obtaining activation of the high-affinity IgE receptor expressed by the cells of the ROSA KIT WT mast cell line, and/or d) the identification of the mediators to be assayed in order to ensure that the activation of said high-affinity IgE receptor has been effective.

Another preferred kit according to the invention, which can be used in the high-throughput tests for screening for molecules aimed at specifically inhibiting the catalytic activity of the KIT D816V receptor, comprises for example: a) at least one product 1 chosen from the ROSA KIT D816V mast cell line, a product derived from said line, chosen from a cell, a cell clone, a cell population, or a cell subpopulation, or a composition according to the invention comprising a product chosen from said line, said cell, said clone, said population and/or said subpopulation, and preferably b) at least one product 2 chosen from the ROSA KIT WT mast cell line, a product derived from said line, chosen from a cell, a cell clone, a cell population, or a cell subpopulation, or a composition according to the invention comprising a product chosen from said line, said cell, said clone, said population and/or said subpopulation, and c) at least one product 3 chosen from the ROSA KIT Delta 417-419 insY mast cell line, a product derived from said line, chosen from a cell, a cell clone, a cell population, or a cell subpopulation, or a composition according to the invention comprising a product chosen from said line, said cell, said clone, said population and/or said subpopulation, and preferably d) written instructions explaining the various steps of the culturing and/or of the preserving of the cells, detailing the composition of the culture medium or media and/or of the preserving medium for the cells and/or listing one or more growth factors which can be used in the context of the culturing and/or of the preserving of said cells, and preferably e) written instructions describing the various steps and/or identifying reagents for measuring the degree of proliferation of each of the three products and for estimating the specificity of the inhibition of the proliferation obtained according to the nature of the KIT receptor borne by one and/or the other of the three products.

The invention also relates to a non-human animal model, typically an immunoinsufficient model, comprising at least one cell or at least one cell population according to the invention, preferably a cell or cell population originating from a mast cell line according to the invention, for example from a cell line exhibiting a KIT receptor mutation, preferably a KIT receptor activating mutation, preferably a cell originating from a line chosen from the ROSA KIT D816V line, the ROSA KIT Delta 417-419 insY line and a line of ROSA KIT D816V or ROSA KIT Delta 417-419 insY type. The invention also relates to a non-human animal model comprising a tumour formed by a cell according to the invention.

Such models can be advantageously used for evaluating, in vivo, the interest, in particular the preventive or therapeutic interest, of a candidate molecule; for verifying the effectiveness in terms of prevention or therapeutic treatment of the molecules identified using the cell tools described in the present invention, which can be used in vitro; or for verifying, in vivo, the possible toxicity of said molecules.

Mast cells are immune system cells which are involved in the inflammatory response, in particular in allergy and hypersensitivity phenomena. They are located in the connective tissue, in particular in the skin, the digestive tract and the respiratory tract, and in the intestinal and respiratory mucosa. There is also a small number of mast cells in the bone marrow and in the lymphoid organs.

Mature mast cells, whatever their location, have certain characteristics in common, such as the presence of numerous metachromatic intra-cytoplasmic granulations (i.e., capable of turning toluidine blue purplish red owing to the presence of heparin in said granulations). They are rounded cells with a diameter of 13 to 22 mm; they have a single rounded nucleus which is central or most commonly off-centre. The cytoplasma is entirely filled with granulations capable of covering the nucleus owing to their abundance.

These granulations contain various chemical substances synthesized by mast cells, in particular histamine, serotonin, proteoglycans such as heparin or chondroitin sulfate, enzymes, in particular proteases, cytokines such as TNF-alpha, and factors which are eosinophil and neutrophil "chemoattractants" (Abraham and Malaviya, Infection and Immunity, 65, 3501, 1997). These pro-inflammatory substances are abruptly released (a phenomenon known as "degranulation") during mast cell activation. In a second step, a secondary response is set up, linked to the de novo synthesis of mediators such as leukotrienes, prostaglandins or PAF (Platelet Activating Factor), but also of interleukins (IL4, IL5, IL6, IL10, IL12, IL13), cytokines (TGF-beta, IFN-gamma, GM-CSF) and chemokines (MCP-1, IL8, RANTES) (Moqbel et al., Immunology, 60, 425, 1987; Befus, Reg. Immunol., 2, 176, 1989). All of these factors actively participate in the triggering of an inflammatory process and the setting up of a T-lymphocyte-dependent specific immune response.

Mast cells in fact constitute a very heterogeneous cell population. Indeed, two distinct mast cell subpopulations which have very different biochemical and functional characteristics have been characterized: mucosal mast cells and serous mast cells. These two subpopulations can be distinguished by the active substances produced and stored in the granules. Thus, in mice, mucosal mast cells produce mainly histamine, chymase and chondroitin sulfate A and E, and serous mast cells produce mainly histamine, serotonin, chymase, tryptase and heparin. In humans, mucosal mast cells, also known as MCT (tryptase+), produce mainly histamine, tryptase, heparin and chondroitin sulfate A and E, and serous mast cells, also known as MCTC (tryptase+ and chymase+) additionally produce chymase.

Mast cells are derived from haematopoietic precursors (Galli, Lab. Invest. 62, 5-33, 1990). Mast cell populations can be obtained from mouse bone marrow cultures in the presence of media conditioned with stimulated T lymphocytes or in the presence of interleukin-3 (IL-3) (Razin, E. et al., J Immunol. 1984 March, 132(3): 1479-86). A pure population of mast cells of mucosal type is thus obtained from a suspension of mouse haematopoietic cells in three weeks by culturing in the presence of IL-3. The inventors have also shown that it is possible to obtain pure populations of serous mast cells in mice by growing the cells of the peritonea of these animals in the presence of Stem Cell Factor (Malbec et al., J Immunol 2007, 178(10): 6465-75).

The obtaining of human mast cell cultures in vitro has proved to be more difficult. Cultures of bone marrow cells or of umbilical cord cells in the presence of IL-3 have resulted in the appearance of basophilic granulocytes (Tadokoro et al., J. Exp. Med., 158, 857-871, 1983). The coculturing of human umbilical cord cells with mouse 3T3 fibroblasts has, however, made it possible to obtain mature mast cells after four weeks of culturing (Furitsu et al. Proc. Natl., Acad. Sci. USA, 86, 10039-10043, 1989). The inventors have subsequently demonstrated that the differentiation and proliferation of human mast cells in vitro depends on the presence of Stem Cell Factor (SCF), which is a ligand of the KIT receptor (Valent, Immunol Today, 15, 111-114, 1994). It is thus possible to obtain virtually pure human mast cell populations by primary culture of CD34+ progenitors from bone marrow or umbilical cord blood for 8 to 10 weeks in the presence of human SCF (Yoshikubo et al., Exp Hematol. 2006, 34(3): 320-9).

Mast cell cultures constitute a useful tool for studying the mechanisms involved in various inflammatory and/or immune phenomena, for example in the context of the allergic response, or of the immune response to attack by various pathogens (Varadaradjalou et al., Eur J Immunol. 2003 April, 33(4): 899-906). However, as previously indicated, cultures of human mast cells have to date been successfully differentiated and maintained in vitro only in the form of non-immortalized primary cultures which can be obtained only after a lengthy culturing time and with a high production cost, which is difficult to make compatible with use in high-throughput screening in the search for molecules of interest. In addition, there are currently available only a small number of human mast cell lines, the characteristics of which make them unsuitable for the abovementioned use (Butterfield et al., Leuk Res. 1988, 12(4): 345-55; Kirshenbaum et al., Leuk Res 2003, 27(8): 677-82; Laidlaw et al., J Allergy Clin Immunol. 2011, 127(3): 815-22.e1-5).

During primary culturing of mast cells obtained from CD34+ cells (haematopoietic precursors) of human umbilical cord blood originating from a healthy individual, the inventors have succeeded in isolating and characterizing a novel human mast cell line, identified as "ROSA KIT WT" in the context of the present invention. This line has morphological, ultrastructural, phenotypic and functional characteristics comparable to those of normal human mast cells.

The ROSA KIT WT line is also advantageously negative for the most common infectious agents: HIV, HBs, HBc and *mycoplasma*.

A particular subject of the invention thus relates to the human mast cell line identified in the present text as "ROSA KIT WT" as registered under deposit number CNCM 1-4551 with the CNCM (Collection Nationale de Cultures de Microorganismes [National Collection of Microorganism Cultures] with l'Institut Pasteur, 25, rue du Docteur Roux, F-75724 Paris Cedex 15, France) on 2 Nov. 2011.

As previously indicated, the invention also relates to any cell, any cell clone (for example obtained by the cell line limiting dilution technique), any cell population and any cell subpopulation derived from said "ROSA KIT WT" line, and also any cell line derived from said "ROSA KIT WT" line obtained from such a cell, population, subpopulation or cell clone, which retains at least one characteristic of the ROSA KIT WT line, typically a morphological, ultrastructural, phenotypic or functional characteristic, preferably a functional characteristic, even more preferentially several of said characteristics, more preferably all the characteristics of said line. The invention also relates to any mutant of the "ROSA KIT WT" line which retains at least one characteristic of the ROSA KIT WT line, typically a morphological, ultrastructural, phenotypic or functional characteristic, preferably several of said characteristics, even more preferentially all the characteristics of said line.

Cells considered to be derivatives of a cell line according to the invention are, for example, cells modified by genetic transformation, for example by mutagenesis, using techniques known to those skilled in the art.

The present invention also relates to a human mast cell line, identified in the present text as "line of ROSA KIT WT type", which has at least one, preferably several, of the following morphological, ultrastructural, phenotypic or functional characteristics:

mast cell phenotype,
presence of metachromatic intra-cytoplasmic granulations,
presence of intra-cytoplasmic granulations containing heparin,
presence of intra-cytoplasmic granulations containing histamine, tryptase, beta-hexosaminidase and/or histidine decarboxylase (HDC),
expression of the wild-type KIT receptor (also identified as CD117, wild-type KIT or WT KIT in the present text) and possible activation of the mast cell by this receptor,
expression of the high-affinity IgE receptor (also identified as FcεR1 or FcepsilonR1 in the present text) and possible activation of the mast cell by this receptor,
expression of the CD33, CD203c, CD300a, CD4 and/or CD9 markers (characteristic of the phenotype of the human mast cells isolated from various tissues of healthy human subjects), preferably of the CD33, CD203c and CD300a markers,
dependence with respect to Stem Cell Factor (SCF) for its survival and growth, typically in the context of a continuous culture,
has a short doubling time, of at most 72 hours, typically of approximately 48 hours, compatible with the rapid obtaining of a large number of cells (which can be used in the context of a method for high-throughput in vitro screening of large chemical libraries);
increase in FcεR1 expression by a treatment with interleukin 4 (IL-4) and/or with human IgEs,
decrease in CD117 expression by treatment with interleukin 4 (IL-4),
immediate increase in the membrane expression of CD203c and/or immediate release of histamine, of beta-hexosaminidase and/or tryptase, and preferably delayed release of TNF-α, by activation preferably:
i) in the presence of specific IgE and of the antigen capable of binding to said specific IgE,
ii) in the presence of IgE and of anti-IgE,
iii) in the presence of anti-FcεR1 receptor antibody,
iv) in the presence of a ligand of another receptor, chosen for example from a TLR ("Toll-Like Receptor"), such as TLR-2, TLR-3, TLR-4 or TLR-9; a receptor for a complement fraction (for example a receptor for a C3 fraction and/or a C5 fraction of complement); and a cytokine or chemokine receptor, and/or
v) in the presence of a non-specific activator (such as the calcium ionophore A23187).

A preferred subject of the invention is a human mast cell line which has all the morphological, ultrastructural, phenotypic and functional characteristics identified above.

A particular subject of the present invention relates, moreover, to a human mast cell line of ROSA KIT WT type, having at least one, typically several, and preferably all of the following morphological, ultrastructural and/or phenotypic characteristics: i) presence of metachromatic intra-cytoplasmic granulations, and ii) expression of the FcεR1 and wild-type KIT (CD117) receptors and of the CD33, CD203c and CD300a markers.

Another particular subject of the present invention relates to a human mast cell line of ROSA KIT WT type which has the following functional characteristics: i) dependence, preferably strict dependence, with respect to SCF for its survival and growth, ii) doubling time of at most 72 hours, preferably of approximately 48 hours, iii) FcεR1 expression increased by treatment with interleukin 4 (IL-4) and/or with human IgEs, iv) CD117 expression decreased by treatment with interleukin 4 (IL-4), and v) immediate increase in the membrane expression of CD203c and/or immediate release of histamine, of beta-hexosaminidase and of tryptase, and delayed release of TNF-α, by activation:
i) in the presence of specific IgE and of the antigen capable of binding to said specific IgE,
ii) in the presence of IgE and of anti-IgE, and/or
iii) in the presence of anti-FcεR1 receptor antibody.

The present invention also relates, as previously indicated, to any cell line derived from the human mast cell line of ROSA KIT WT type described above and any cell clone or mutant of said line, said derived cell line, cell clone and mutant having retained at least one, preferably several (for example at least one phenotypic characteristic and at least one functional characteristic), and ideally all of the morphological, ultrastructural, phenotypic and/or functional characteristics identified above, which are characteristic of said human mast cell line of ROSA KIT WT type.

The ROSA KIT WT line and the lines of the ROSA KIT WT type have a KIT receptor of normal structure, have a short doubling time of approximately 48 hours, can be repeatedly frozen and thawed by conventional methods known to those skilled in the art (the freezing-thawing not causing any morphological and/or functional modification of the cells) and have a low production cost, thereby making it possible for them to be produced in large amounts and for them to be used in high-throughput screening tests.

The ROSA KIT WT line and the lines of the ROSA KIT WT type, like their clones (cf. clones isolated, analysed, and identified by the inventors as "ROSA 1" to "ROSA 8"), have the capacity to proliferate in basic culture medium (for example RPMI-1640 with 10% foetal calf serum) supplemented with cytokine, typically with SCF, while at the same time retaining their morphological, ultrastructural, phenotypic and functional characteristics, which further reduces the cost of production of the cells in large amounts.

The ROSA KIT WT line and the lines of the ROSA KIT WT type are also advantageously capable of maturing during coculturing with sublayers of stromal cells, preferably during long-term coculturing (typically more than 30 days) with such sublayers. The inventors have thus grown the ROSA KIT WT line on a sublayer of mice stromal cells (MS-5 line) and have demonstrated that this treatment induces a very significant differentiation of the cells of the ROSA KIT WT line, which is reflected, for example, by a very clear increase in the number of granulations in the cells, associated with a significant decrease in the nucleus surface/cell surface ratio.

The cells and lines according to the invention can also, as previously indicated, advantageously be activated by the IgE-anti IgE pairing or by a specific IgE-corresponding allergen pairing and can therefore be used, for example, for physiopathological studies of the mechanisms of allergy and for developing and/or implementing high-throughput molecule screening tests in the search for anti-allergic properties. The activation of mast cells by such a pairing results in degranulation with immediate release typically of histamine and of beta-hexosaminidase, said release being conventionally associated with a signficant increase in the membrane expression of CD203c, and with a delayed release of TNF-alpha. The various events of this cascade can easily be demonstrated and measured in the context of a method according to the invention as described later in the present text, by means of techniques known to those skilled in the art. The cells and lines according to the invention can, moreover, be activated by other molecules capable of specifically or non-specifically targeting other membrane receptors of mast cells, for example a TLR2 receptor ligand (such as peptidoglycan or PGN), a TLR4 receptor ligand (such as lipopolysaccharide or LPS), or a non-specific activator (such as the calcium ionophore A23187).

Another subject of the invention relates to a method for preparing a population of human mast cells of which at least 80% of the cells, preferably at least 95%, more preferentially at least 98%, entirely preferably at least 99%, and ideally 100% of the cells have the characteristics of the cells of a human mast cell line according to the invention, preferably the following characteristics:
i) possible proliferation during a period greater than six months,
ii) containing granulations containing histamine, tryptase and/or heparin, and
iii) expressing the wild-type KIT receptor (CD117 or WT KIT) and the FcεR1 receptor.

This method comprises culturing haematopoietic precursors or progenitors, preferably stem cells, originating from the umbilical cord blood of a healthy human subject, in a culture medium comprising at least 5 ng/ml, preferably at least 25 ng/ml, more preferentially at least 50 ng/ml, typically between approximately 50 ng/ml and approximately 200 ng/ml, for example approximately 60 ng/ml, 65 ng/ml, 70 ng/ml, 75 ng/ml, 100 ng/ml, 125 ng/ml, 150 ng/ml or 175 ng/ml, entirely preferably approximately 80 ng/ml, of human Stem Cell Factor (SCF) for a period of time sufficient to obtain the population of human mast cells having the desired characteristic(s).

According to one preferred embodiment of the present invention, the cells are grown in this medium for at least 2 days (48 hours), for example 72 hours, typically between 30 and 100 days, preferably between 50 and 70 days, so as to obtain a pure (100% mast cells) or substantially pure (99% mast cells) population of mast cells. The cells can subsequently be kept in culture ("maintained") in the same medium for as long as desired by those skilled in the art.

The method according to the invention thus makes it possible to obtain a population of human mast cells which is more or less pure according to the duration of culturing of the cells, preferably a human mast cell line. The resulting cells advantageously retain the characteristics of the mast cells of origin.

A particular subject of the invention thus relates to a primary culture of mast cells obtained from haematopoietic precursors or progenitors originating from the umbilical cord blood of a healthy ("normal") human subject whose mast cells express a normal KIT receptor (VVT KIT), i.e., a functional receptor which has a normal structure.

Such a method typically makes it possible, by means of successive passages in the presence of human SCF, to prepare the ROSA KIT WT human mast cell line and the lines of the ROSA KIT WT type according to the invention.

According to one particular embodiment of the method according to the invention, it is possible to obtain mast cells which express the high-affinity IgE receptor (FcεR1) in high numbers by providing for, in the method described above, a step of bringing the haematopoietic precursors into contact with interleukin 4 (IL-4) (for example 20 ng/ml for four to five days) and/or monomeric IgEs (for example 10 μg/ml for four to five days).

The expression level of the FcεR1 receptors can be measured by means of the flow cytometry method, typically after immunolabelling with an anti-FcεR1 antibody combined with a fluorochrome such as FITC (fluorescein isothiocyanate 1) or APC (allophycocyanin). The rise in the number of FcεR1 receptors increases the level of degranulation of the cells stimulated:
i) in the presence of specific IgE and of the antigen capable of binding to said specific IgE,
ii) in the presence of IgE and of anti-IgE, and/or
iii) in the presence of anti-FcεR1 receptor antibody.

Moreover, the invention covers any cell, cell population, cell subpopulation, human mast cell line or cell clone which can be obtained at the end of a method according to the invention.

According to yet another embodiment according to the invention, the method also comprises a step of transforming the cells in culture with a nucleic acid responsible for the expression, by the cell, of a mutated KIT receptor.

The nucleic acid is preferably an oncogene encoding a mutated KIT receptor, the function of which is modified. It is typically a KIT receptor which has an abnormal structure. The mutation may inhibit the normal function of KIT or, on the contrary, activate it, for example activate it constitutively. It is preferably a KIT-activating mutation associated with a pathological condition in which mast cells are involved, for example a pathological condition in which mast cells have a deleterious role. It is typically a KIT receptor-activating mutation associated with a pathological condition preferably chosen from mastocytosis, acute leukaemia, lymphoma and a solid tumour.

The oncogene may, for example, be an oncogene encoding D816V-mutated KIT or encoding the mutated KIT Delta 417-419 insY (two KIT abnormalities frequently encountered in mastocytoses), respectively known as "KIT D816V oncogene" and "KIT Delta 417-419 insY oncogene". Such an oncogene is immortalizing, i.e., it makes it possible to culture the transformed cells in an SCF-free medium.

The invention thus relates to a method for preparing a mast cell line exhibiting a KIT receptor mutation, comprising the transformation of a human mast cell line according to the invention, typically of a cell line of ROSA KIT WT type, by introducing, into the cells of said line, a nucleic acid encoding a mutated KIT receptor, so as to obtain a mast cell line exhibiting said KIT mutation, typically by means of an expression vector. Advantageously, this method may also comprise a step of selecting the cells actually transformed (for example by demonstrating the expression of a reporter gene introduced into the cells at the same time as the oncogene).

In one preferred embodiment of the method of the invention, the expression vector is a retroviral vector, preferably a lentiviral vector. This vector can be easily chosen by those skilled in the art from the vectors which allow the expression of a transgene in mammalian cells. The reporter gene can also be easily selected by those skilled in the art from the genes encoding known markers such as luciferase, GFP (Green Fluorescent Protein) and its derivatives such as EGFP, proteins emitting a blue fluorescence (EBFP, EBFP2, Azurite, mKamala1), proteins emitting a cyan or light blue fluorescence (ECFP, Cerulean, CyPet), proteins emitting a yellow fluorescence (YFP, Citrine, Venus, YPet), DsRed and its derivatives, Keima and its derivatives, glucuronidase (GUS), beta-glucosidase, alkaline phosphatase, horseradish peroxidase (HRP) and beta-galactosidase (LacZ).

Such a method makes it possible to obtain a cell population, in particular a mast cell line, exhibiting a KIT mutation. When the mutation is a KIT-activating mutation, the method makes it possible to obtain mast cells expressing a constitutively activated KIT receptor.

One particular subject of the invention thus relates to a mast cell line which can be obtained at the end of the method described above, or a derived cell line, a cell clone or a mutant of said line having retained at least one characteristic of said line, typically a morphological, ultrastructural, phenotypic or functional characteristic, preferably several of said characteristics, even more preferentially all the characteristics of said line.

Such a line exhibits a KIT receptor mutation. Advantageously, this mutation may be responsible i) for the acquisition, by the line, of independence with respect to SCF for its survival and its growth; ii) for the acquisition, by the line, of in vivo tumorigenicity in mammals; iii) for an increase in the capacity of the line to release a mediator of inflammation or of allergy in the presence of specific IgE and of the antigen capable of binding to said specific IgE, in the presence of IgE and of anti-IgE, or in the presence of anti-FcεR1 receptor antibody, or by activation of a receptor of the TLR type, of a complement fraction receptor, or of a cytokine chemokine receptor; iv) for a change, typically an activation, of the intra-mast cell signalling in the line; and/or v) for an interaction of said mutated KIT receptor or of at least one of its signalling pathways with at least one other mast cell receptor or at least one of its signalling pathways.

The invention also relates to any derived cell line, cell clone or mutant of such a human mast cell line according to the invention exhibiting a KIT receptor mutation, having retained at least one, preferably several, and ideally all of its morphological, ultrastructural, phenotypic and/or functional characteristics, preferably its functional characteristics.

The inventors have thus transfected cells of the ROSA KIT WT line with lentiviral vectors providing a nucleic acid sequence SEQ ID NO: 3 encoding the D816V-mutated KIT receptor (SEQ ID NO: 4) or providing a nucleic acid of SEQ ID NO: 5 encoding the mutated KIT receptor Delta 417-419 insY (SEQ ID NO: 6), and have been able to establish two other novel lines which are SCF-independent in terms of their proliferation, i.e., the lines identified in the present text as "ROSA KIT 0816V" and "ROSA KIT Delta 417-419 insY". These lines, which are particularly easy to grow in large amounts, have a phenotype which is very close to that of the abnormal mast cells encountered during mastocytoses.

One particular subject of the invention thus relates to the human mast cell line identified in the present text as "ROSA KIT D816V" as registered under deposit number CNCM 1-4552 with the CNCM on 2 Nov. 2011, derived from the ROSA KIT WT human mast cell line. As previously indicated, the invention also relates to any cell, any cell clone, any cell population and any cell subpopulation derived from said "ROSA KIT D816V" line, and also to any cell line derived from said "ROSA KIT D816V" line obtained from such a cell, population, subpopulation or clone, which retains at least one characteristic of the ROSA KIT D816V line, typically a morphological, ultrastructural, phenotypic or functional characteristic, preferably several of said characteristics, and even more preferentially all the characteristics of said line. The invention also relates to any mutant of the "ROSA KIT D816V" line which retains at least one characteristic of the ROSA KIT D816V line, typically a morphological, ultrastructural, phenotypic or functional characteristic, preferably several of said characteristics, and even more preferentially all the characteristics of said line.

The present invention also relates to a human mast cell line derived from the ROSA KIT WT line, identified in the present text as "line of ROSA KIT D816V type", having at least one, preferably several, and even more preferentially all of the following morphological, ultrastructural, phenotypic or functional characteristics:

growth totally independent of the presence of cytokine, SCF in particular,
culturing possible in inexpensive culture media, for instance RPMI-1640 containing 10% of foetal calf serum,
mast cell phenotype,
simultaneous expression of the CD33, CD203c and CD300a markers (characteristic of the phenotype of human mast cells),
expression of the KIT receptor exhibiting the D816V mutation (the membrane expression of KIT being significantly higher than in the ROSA KIT WT parental line),
expression of KIT D816V messenger RNAs,
expression of a functional FcepsilonR1 receptor (the aggregation by the IgE-anti IgE pairing inducing membrane overexpression of CD203c demonstrates the functional nature of the FcεR1 receptor),
presence of intra-cytoplasmic granulations containing histamine, tryptase, beta-hexosaminidase and/or histidine decarboxylase,
fast doubling time of at most 72 hours, typically of approximately 48 h,
can be easily frozen and thawed using conventional methods known to those skilled in the art,
capacity to form colonies in semi-solid medium, said colonies, when they are individually retransferred into the liquid medium, being themselves capable of giving rise to subclones of the parental line, and
resistance to imatinib and sensitivity to dasatinib in terms of proliferation inhibition.

Another particular subject of the invention relates to the human mast cell line identified in the present text as "ROSA KIT Delta 417-419 insY" as registered under deposit number CNCM I-4553 with the CNCM on 2 Nov. 2011, derived from the ROSA KIT WT human mast cell line. As previously indicated, the invention also relates to any cell, any cell clone, any cell population and any cell subpopulation derived from said "ROSA KIT Delta 417-419 insY" line, and also any cell line derived from said "ROSA KIT Delta 417-419 insY" line obtained from such a cell, population, subpopulation or clone, which retains at least one characteristic of the ROSA KIT Delta 417-419 insY line, typically a morphological, ultrastructural, phenotypic or functional characteristic, preferably several of said characteristics, and even more preferentially all the characteristics of said line. The invention also relates to any mutant of the "ROSA KIT Delta 417-419 insY" line which retains at least one characteristic of the ROSA KIT Delta 417-419 insY line, typically a morphological, ultrastructural, phenotypic or functional characteristic, preferably several of said characteristics, and even more preferentially all the characteristics of said line.

The present invention also relates to a human mast cell line derived from the ROSA KIT WT line, identified in the present text as "line of ROSA KIT Delta 417-419 insY type", which has at least one, preferably several, and even more preferentially all of the following morphological, ultrastructural, phenotypic or functional characteristics:

growth totally independent of the presence of cytokine, SCF in particular,
culturing possible in inexpensive culture media, for instance RPMI-1640 containing 10% of foetal calf serum,
mast cell phenotype, simultaneous expression of the CD33, CD203c and CD300a markers (characteristic of the phenotype of human mast cells), expression of the KIT receptor exhibiting the Delta 417-149 insY mutation (the membrane expression of KIT being significantly higher than in the ROSA KIT WT parental line), expression of KIT Delta 417-149 insY messenger RNAs, expression of a functional FcepsilonR1 receptor (the aggregation by the IgE-anti IgE pairing inducing membrane overexpression of CD203c demonstrates the functional nature of the FcεR1 receptor), presence of intra-cytoplasmic granulations containing histamine, tryptase, beta-hexosaminidase and/or histidine decarboxylase, fast doubling time of at most 72 hours, typically of approximately 48 h, can be easily frozen and thawed using conventional methods known to those skilled in the art, capacity to form colonies in semi-solid medium, said colonies, when they are individually retransferred into liquid medium, being themselves capable of giving rise to subclones of the parental line, and sensitivity to imatinib and dasatinib in terms of proliferation inhibition.

The "ROSA KIT D816V" and "ROSA KIT Delta 417-419 insY" lines and also the lines of ROSA KIT D816V or ROSA KIT Delta 417-419 insY type proliferate autonomously and can advantageously be grown in an SCF-free medium, as indicated above.

Other methods, distinct from transfection by antiviral vectors and known to those skilled in the art, can be used to obtain the transformation of the cells, such as electroporation (Neumann E et al. (1982), *EMBO J.* 1 (7): 841-5) or lipofection (Feigner P L et al. (1987) *Proc Natl Acad Sci USA* 84: 7413-7417).

The invention also relates to a method for obtaining or isolating clonal cells, comprising the limiting dilution of a cell line according to the invention.

The invention also relates to cell clones derived from the ROSA line exhibiting, respectively, the KIT-activating mutations most frequently encountered in mastocytoses (KIT D816V and KIT Delta 417-419 insY).

Also considered to be subjects of the present invention are the derived mast cell lines, and also the cell clones and the mutants (natural or obtained artificially) of said ROSA KIT WT, ROSA KIT D816V and Delta 417-419 insY lines, having retained at least one, preferably several, and even more preferentially all of their characteristics.

Moreover, the invention relates to a non-human animal model comprising at least one cell originating from a mast cell line according to the invention, preferably from a line chosen from the ROSA KIT D816V line, the ROSA KIT Delta 417-419 insY line and the line of ROSA KIT D816V or ROSA KIT Delta 417-419 insY type. It also relates to the use of such a line for evaluating, in vivo, the interest, in particular the preventive or therapeutic interest, of a candidate molecule.

The cells according to the invention represent progress in economic terms since they are easy to manipulate, grow and amplify in very large amounts using inexpensive reagents and materials. They can advantageously be used, in particular, in research or in the context of high-throughput methods of screening for molecules of interest. The animal models according to the invention which comprise such cells can themselves advantageously be used, in particular, for verifying the effectiveness of the molecules screened with respect to the prevention or treatment of pathological conditions in which mast cells play a role, in particular perform a deleterious role (mastocytoses for example).

The cells and cell lines according to the invention can be used as a research tool, in particular as cell models.

They are of quite particular interest as an in vitro model for studying the cellular and/or intracellular mechanisms which are involved in the activation of these cells. The mast cells according to the invention can thus be used for testing, in vitro, the mast cell activation capacity of an agent or a molecule of interest or, on the contrary, its capacity to inhibit mast cell activation, in particular the IgE-dependent activation of said cells, mediated by the high-affinity IgE receptor, or mast cell activation mediated by the KIT receptor, using techniques known to those skilled in the art. It is also possible to use these cells for testing the capacity of an agent or a molecule of interest to modulate (i.e., activate, inhibit or modify) the tumorigenicity, clonogenicity, survival, apoptosis, proliferation, differentiation, activation, function, phenotype, morphological appearance and/or ultrastructural appearance of human mast cells.

The mast cells and lines according to the invention can thus be used for studying mast cell activation in response to a substance chosen, for example, from an allergen, a microorganism (for example, a bacterium, a virus and/or a parasite) and a product derived from one of these microorganisms.

The cells and cell lines according to the invention can also be used, for example, in the context of physiopathological studies relating in particular to the pathological conditions mentioned in the present description, or for the high-throughput screening for molecules of interest. They can be used in particular for screening for molecules which specifically target the high-affinity IgE receptor, the signalling pathway induced by the activation of the high-affinity IgE receptor, the (normal or mutated) KIT receptor, the cell signalling pathway induced by the activation of the normal KIT receptor or an abnormal cell signalling pathway induced by the activation of a mutated KIT receptor (for example, KIT D816V and KIT Delta 417-419 insY), in the latter case, for example, for identifying molecules which have antiproliferative properties.

The cells and lines of the invention can also be used for screening for an agent or a molecule of interest which is of use in the prevention, diagnosis, treatment and/or follow-up of a pathological condition, typically a pathological condition in which mast cells play a beneficial or deleterious role.

The pathological condition targeted is preferably chosen from an allergy, an inflammatory disease, an autoimmune disease, an infection, non-allergic asthma, urticaria and a tumour, typically a mastocytosis, a myeloid hemopathy, for example acute myeloid leukaemia, lymphoma and a solid tumour, for example a gastrointestinal stromal tumour (GIST).

The mast cells according to the invention can also, for example, be used in a method according to the invention of screening for vaccine antigens or diagnostic reagents.

They can also be used for identifying novel biomarkers for diagnosing a pathological condition in which mast cells have a beneficial or deleterious role, or for novel biomarkers indicating sensitivity or, on the contrary, resistance to a molecule used in the treatment or prevention of such a pathological condition.

The identification of such biomarkers can be carried out by analysis of the expression profiles of cells sensitive to a particular known molecule, different cells resistant to the same molecule and/or cells resistant to various known molecules. The identification can also be carried out by RT-PCR, Western blotting, immunohistochemistry, etc.

The molecule of interest may be a molecule which has a cytotoxic or cytostatic effect on the cells. Alternatively, it may be a molecule which increases the therapeutic efficacy of another molecule used as a medicament, a molecule which increases or restores the sensitivity of the cells to a molecule to which they are resistant, a molecule which prevents, reduces or delays the appearance of such a resistance, or a molecule which enables an alternative treatment with respect to the existing treatments.

The molecule of interest may be a natural, recombinant or synthetic molecule.

The molecule which may be tested can be chosen, for example, from a chemical molecule, a polypeptide, a protein, a nucleic acid (for example, an siRNA, a ribozyme, etc.) and/or an antibody. Various doses of the molecule can be tested using the same method.

The mast cells according to the invention can also be used for testing, in vitro, the impact of a therapeutic treatment chosen from exposure to radiation (for example, radiotherapy), chemotherapy, immunotherapy, gene therapy, and any combination of these treatments.

The methods according to the invention, described below, which use cells or cell populations according to the invention, in particular cell lines according to the invention, illustrate examples of possible applications of the products according to the invention.

Each method described in the present text can obviously comprise, when the text below does not indicate it, a step of application, to control cells, of the treatment described for the cells studied, for the purposes of comparison, this step being carried out identically, but in the absence of the molecule to be tested when it is a negative control, or in the absence of a molecule known for its effectiveness with respect to the parameter to be tested when it is a positive control.

A method according to the invention makes it possible to evaluate the capacity of at least one candidate molecule to modulate the tumorigenicity, clonogenicity, survival, apoptosis, proliferation, differentiation, activation, function, phenotype, morphological appearance and/or ultrastructural appearance of human mast cells. This method comprises:
a) bringing a cell, a cell clone, a cell line, a mast cell population, a cell subpopulation or a composition according to the invention, typically a mast cell line, into contact with at least one candidate molecule as previously defined; and
b) determining, using techniques known to those skilled in the art, the tumorigenicity, clonogenicity, survival, apoptosis, proliferation, differentiation, activation, function, phenotype, morphological appearance and/or ultrastructural appearance of the mast cells belonging to said line, cell, cell clone, cell population, cell subpopulation, or composition exposed to said at least one candidate molecule, said determining making it possible to evaluate the corresponding capacity of said at least one candidate molecule to modulate the tumorigenicity, clonogenicity, survival, apoptosis, proliferation, differentiation, activation, function, phenotype, morphological appearance and/or ultrastructural appearance of human mast cells.

The determining of the tumorigenicity of the mast cells can be carried out, for example, by injecting one or more of these cells subcutaneously or intravenously into immuno-suppressed mice (SCID, NOD-SCID and/or NSG mice) sublethally irradiated beforehand. According to the type of injection, the mice are sacrificed either when a subcutaneous tumour appears at the point of injection, or when the general condition of the mouse is impaired (in the case of intravenous injection). The mast cell nature of the proliferation can then be confirmed by specific immunohistochemical or immunocytochemical labelling of the tumour cells (positivity for tryptase and human CD45), either at the level of the cells of the subcutaneous tumour (in the case of subcutaneous injection) or at the level of the medullary cells (in the case of intravenous injection).

The determining of the clonogenicity of the mast cells can be carried out, for example, by culturing a predetermined number of these cells in semi-solid medium based on methylcellulose or agar in a Petri dish, and measuring the number of clones or of colonies obtained after a variable incubation time (preferentially between 7 and 21 days) in an incubator at 37° C. and 5% $CO_2$ in air.

The determining of the survival, of the apoptosis and/or of the proliferation of the mast cells can be carried out, respectively, by determination of the percentage of live cells after staining with a vital dye such as trypan blue; by cytofluorimetric determination of the percentage of apoptotic cells having bound FITC-labelled annexin V; and by determination that the reduction of tetrazolium salts or MTT technique (tetrazolium yellow MTT (3-(4,5-dimethylthiaz-olyl-2)-,5-diphenyltetrazolium)) is reduced in cells which are metabolically active, and therefore which proliferate, partly through the action of enzymes of the dehydrogenase type. The resulting intracellular formazan gives a purple precipitate which can be dissolved and quantified by spectrophotometric measurement.

The determining of the differentiation of the mast cells can be evaluated by demonstration of markers of human mast cell differentiation, such as an increase in the number of metachromatic intra-cytoplasmic granulations, an increase in the expression of the high-affinity IgE receptor (FcεRI) and/or the appearance of a positivity for chymase (i.e., production of chymase by the mast cells).

The determining of the activation of the mast cells can be evaluated by demonstration of the release of mediators as defined below in the description.

The modulation of the function of the mast cells can be demonstrated, for example, but not solely, by the capacity of these cells to encompass and to destroy bacteria or viruses, or by the capacity of these cells to present the antigen to other cells of the immune system, using techniques known to those skilled in the art.

The determining of the phenotype and of the morphological appearance of the mast cells can be carried out by optical or electron microscopy and the determining of the ultrastructure of the mast cells by electron microscopy.

Another method according to the invention makes it possible to determine the capacity of a candidate molecule to interfere with the binding of at least one ligand or of at least one substrate to at least one human mast cell receptor or to at least one other mast cell substrate; to modulate (i.e., to activate, inhibit or modify as previously indicated) the transduction of at least one signal in a human mast cell; and/or to modulate the synthesis and/or the release of at least one mediator by a human mast cell. This method comprises:
a) bringing a cell, a cell clone, a cell line, a mast cell population, a cell subpopulation or a composition according to the invention, typically a mast cell line, into contact with at least one candidate molecule as previously defined, and
b) demonstrating or measuring i) binding of at least one ligand or at least one substrate to at least one human mast cell receptor or to at least one other mast cell substrate, ii) the synthesis or the release of at least one mediator by a human mast cell, and/or iii) the transduction of at least one signal in the mast cells of said line, of the cell, of the cell clone, of the cell population, of the cell subpopulation or of the composition, so as to determine, respectively, i) the capacity of said at least one candidate molecule to interfere with the binding of at least one ligand or of at least one substrate to at least one receptor present at the surface of a human mast cell or to at least one other mast cell substrate, ii) to modulate the synthesis or the release of at least one mediator by a human mast cell and/or iii) to modulate the transduction of at least one signal in a human mast cell.

The term "human mast cell receptor" is intended to mean the receptors present at the surface of mast cells and also the receptors present in mast cells which are involved in the transmission of at least one intracellular signal initiated by the activation of the receptor.

Receptors present at the surface of mast cells are, for example, FcεR1, KIT WT, FcγR1, TLR2, TLR3, TLR4, $CA_3R$, $EP_{3/4}$, $A_3R$, CCR1 and CCR1/5. The receptor may be a mutated receptor, for example a mutated KIT receptor.

Receptors present inside mast cells are, for example, but not solely, cytoplasmic receptors capable of specifically binding a steroid hormone such as testosterone, oestradiol, progesterone, cortisone, or aldosterone; a thyroid hormone; vitamin D3; and retinoic acid derivatives.

A preferred method according to the invention makes it possible to determine the capacity of a candidate molecule to interfere with the binding of at least one ligand or of at least one substrate to at least one receptor chosen from FcεR1, WT KIT, and a mutated KIT receptor as described in the present application.

The term "ligand" is intended to mean any molecule, of any chemical nature whatsoever, capable of specifically binding to a mast cell membrane receptor (for example, but not solely, IgE which binds to its high-affinity receptor, FcεR1, or Stem Cell Factor, which binds to its specific KIT receptor) or to a mast cell cytoplasmic receptor (for example, but not solely, all-trans-retinoic acid, which binds to its receptor, RARalpha, or vitamin D3, which binds to its receptor, VD3R) and capable of inducing, via its binding, a conformational change, an activation, an inhibition, an overexpression, an underexpression and/or a degradation of this receptor.

The term "mast cell substrate" is intended to mean any molecule, of any chemical nature whatsoever, present on the inside, on the outside or in the membrane of the mast cell and capable of being activated directly or indirectly after the binding of a ligand to a mast cell membrane or an intracytoplasmic or nuclear receptor (for example, but not solely, the Syk protein molecule, which is a substrate of the FcεR1 receptor and which is recruited when this receptor is activated, or the STAT-5 molecule, which is the substrate of the JAK2 molecule, itself recruited and activated during activation of the KIT receptor).

The term "signal" is intended to mean any intracellular, membrane or extracellular event generated by the activation of a mast cell membrane and/or intracellular receptor and which induces mast cell differentiation, proliferation, apoptosis, activation and/or migration.

The term "mediator" denotes any substance, of any chemical nature whatsoever, stored in the granulations or the cytoplasm (histamine, tryptase, HDC) or neosynthetized (prostaglandin, leukotriene, cytokines such as TNF-alpha and/or chemokines such as interleukin-8) by the mast cell, and released into the cytoplasm, the membrane or the surrounding medium of the mast cell, spontaneously or after activation of this cell.

The demonstration or the measurement of binding of a ligand or of a substrate to a human mast cell receptor or to another mast cell substrate can be carried out, for example, by using a ligand, a radioactive substrate, a fluorescent substrate, or a substrate labelled with an enzyme, and/or by coordinated immunoprecipitation of the ligand and/or of the substrate and of the receptor and/or of another substrate or of another ligand.

The demonstration or the measurement of the synthesis or of the release of a mediator by a human mast cell can be carried out, for example, by direct measurement of the mediator on the inside or the outside of the mast cell using an immunolabelling technique or an immunoenzymatic technique (ELISA) specific for the mediator, or a liquid-phase or gas-phase chromatography technique.

The demonstration or the measurement of the transduction of a signal in the mast cells can be carried out, for example, by means of the Western blotting technique using one or more antibodies specific for one or more intracytoplasmic or intranuclear substrates. These antibodies can recognize the substrate(s) in native form or in activated form (for example, but not solely, in phosphorylated form). Such a technique makes it possible not only to measure the expression level of said substrate(s) in native form and to compare this or these level or levels between cells treated differently, but also to measure the level of activation of said substrate(s) and to compare this or these level or levels between cells treated differently.

In the case of allergy for example, the cells according to the invention, and more particularly the cells derived from the ROSA KIT WT primary culture, can be used in tests for high-throughput screening of libraries of candidate molecules (or test molecules), in the search for molecules which inhibit the IgE dependent activation of said cells.

Another method according to the invention makes it possible to determine the capacity of a candidate molecule to increase or to decrease the survival and/or the proliferation, and/or to inhibit or induce the apoptosis, of human mast cells. This method comprises:
a) bringing a cell, a cell clone, a cell line, a mast cell population, a cell subpopulation or a composition according to the invention, typically a mast cell line, into contact with at least one candidate molecule as previously defined; and
b) determining the level of survival and/or of proliferation and/or of apoptosis of the mast cells of said line, of the cell, of the cell clone, of the cell population, of the cell subpopulation, or of the cells in the composition, an increase or a decrease in the survival and/or the proliferation and/or the inhibition or the induction of the apoptosis of said cells determining the capacity of the at least one candidate molecule to respectively increase or decrease the survival and/or the proliferation and/or to inhibit or induce the apoptosis of human mast cells.

The determining or the measuring of the level of survival can be carried out by counting the percentage of live cells after the use of a vital dye such as trypan blue.

The determining or the measuring of the proliferation of the mast cells according to the invention can be carried out by direct measurement of the size of a tumour or by indirect measurement using a fluorescent label such as GFP, the luminescence intensity of which will be proportional to the size of the tumour, and which may be followed in the animal by real-time imaging of the tumour site and/or the whole body.

The determining or the measuring of the apoptosis of the mast cells according to the invention can be carried out by measuring the binding of annexin V. The loss of membrane asymmetry, measured through the binding of annexin V to the phosphatidylserines, can be detected by means of the APOPTEST™-Fluos kit (Dako, France): after exposure, $10^6$ cells are incubated (10-15 min.) in 100 µl of cold labelling solution (1 µl of an annexin-V/FITC and 2.5 µl of propidium iodide (PI) 250 µg/ml) in 96 µl of labelling buffer. 250 µl of labelling buffer are then added and the samples are analysed on a FACScan® flow cytometer.

A molecule capable of decreasing or inhibiting the proliferation or the survival and/or of inducing or of increasing the apoptosis of human mast cells can be used in the prevention or treatment of a tumour as described in the present text, for example of mastocytosis. The efficacy of such a molecule or of several of them can be evaluated in vitro and ex vivo, for example by measuring the level of release of one or more mediators by the mast cells involved in the mastocytosis, typically by the mast cells of a subject suffering from mastocytosis, typically of a human subject, a level of release which is decreased compared with the level observed on the same mast cells not exposed to said molecule(s) revealing the efficacy of said molecule(s).

In the context of mastocytoses for example, the cells according to the invention, and more particularly the cells derived from the ROSA KIT D816V and ROSA KIT Delta 417-419 insY transformed lines, can be used in tests for high-throughput screening of libraries of candidate molecules, in the search for molecules which inhibit the proliferation, the survival and/or the activation of said cells.

The invention also relates to a method for evaluating the toxicity of a candidate molecule capable of or liable to target human mast cells carrying one or more mutations of the KIT receptor, typically a KIT-activating mutation, for example a mutation located in the phosphotransferase domain of the WT KIT receptor (corresponding to the amino acids occupying positions 762 to 937 of SEQ ID NO: 2), such as the D816V (Asp816Val) mutation, the A814V (Ala814Val) mutation or the R815K (Arg815Lys) mutation; in the juxtamembrane domain of the KIT receptor, such as the V559I (Val559Ile) mutation, the V560G (Val560Gly) mutation or the D572A (Asp572Ala) mutation; or in the extramembrane domain of the KIT receptor, such as the KIT Delta 417-419 insY mutation, the KIT S476I (Ser476Ile) mutation, the KIT ITD502-503 mutation ("Internal Tandem Duplication", i.e., repetition twice of amino acids 502 and 503), or the KIT K509I (Lys509Ile) mutation, said method comprising:
a) bringing a cell, a cell clone, a cell line, a mast cell population, a mast cell subpopulation or a composition according to the invention, preferably the ROSA KIT WT mast cell line, into contact with at least one candidate molecule as previously defined, capable of or liable to target human mast cells carrying a mutation of the KIT receptor; and
b) evaluating the possible toxicity of said molecule with respect to said cell, to said cell clone, to said cell line, to said mast cell population, or to said cell subpopulation, preferably to said ROSA KIT WT mast cell line, typically by determining and/or measuring the survival of the cells.

The present invention relates, moreover, to methods for testing the interest, in particular the efficacy in terms of prevention or treatment of a pathological condition, or the toxicity of at least one candidate molecule on animal models according to the invention, comprising a mast cell according to the invention, typically a mast cell population.

The invention thus teaches a particular method for determining the capacity of at least one candidate molecule to prevent or treat at least one tumour and the possible metastases thereof. This method typically comprises:

a) administrating the at least one candidate molecule to an animal model according to the invention, typically a non-human animal model comprising at least one cell originating from a mast cell line according to the invention, preferably from a line chosen from the ROSA KIT D816V line, the ROSA KIT Delta 417-419 insY line and a line of ROSA KIT D816V or ROSA KIT Delta 417-419 insY type; and
b) measuring the proliferation of the cells of said at least one tumour and of said possible metastases of said animal model, an inhibition of or a decrease in the proliferation of said cells in said animal model indicating that the at least one candidate molecule can be used for preventing or treating said at least one tumour and the possible metastases thereof.

Such a method makes it possible to evaluate, in vivo, the interest, in particular the preventive or therapeutic interest, of a candidate molecule screened using one of the methods that can be performed in vitro or ex vivo, described in the present text, which use a cell according to the invention.

Another method according to the invention makes it possible to determine the capacity of a candidate molecule to modulate the infectiousness of at least one infectious agent with respect to human mast cells. This method comprises:
a) bringing a cell, a cell clone, a cell line, a mast cell population, a cell subpopulation or a composition according to the invention, typically a mast cell line, into contact with at least one candidate molecule as previously defined and at least one infectious agent; and
b) determining the capacity of said at least one infectious agent to infect the mast cell, said determining making it possible to determine the capacity of the at least one candidate molecule to modulate the infectiousness of said at least one infectious agent with respect to human mast cells.

The infectious agent may be a microorganism, for example a virus such as the Dengue virus, a bacterium, a fungus or a parasite.

Another method according to the invention makes it possible to determine the capacity of a candidate molecule to modulate the infectiousness of a virus with respect to human mast cells, and also its ability to replicate in a cell according to the invention, by bringing a first population of mast cells infected with said virus into contact with a second population of mast cells not infected with said virus, and determine the capacity of said virus to infect the second population of mast cells.

The following figures and examples illustrate the invention by describing the obtaining of cultures and of human mast cell lines in accordance with the invention, without limiting the scope thereof.

FIGURE LEGENDS

FIG. 1: Characterization of the ROSA KIT WT cells by May-Grünwald Giemsa (MGG) staining, toluidine blue staining and Transmission Electron Microscopy (TEM).

Figure 2:
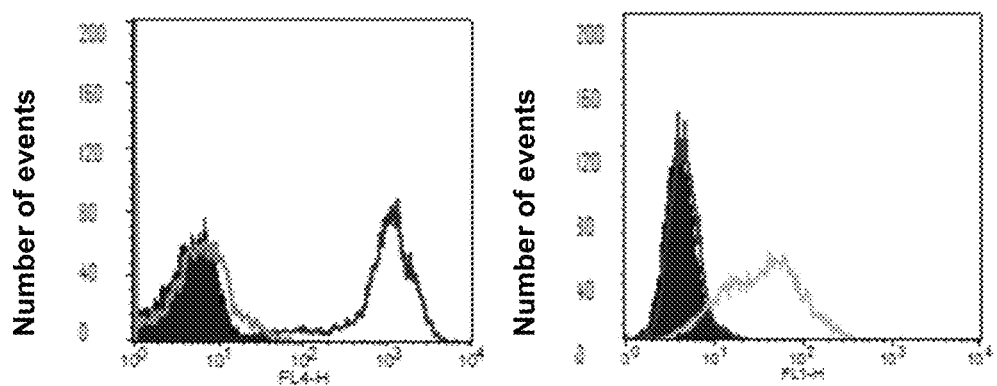

FIG. 2: Expression of the KIT receptor (left-hand histogram) and of the high-affinity IgE receptor (FcεR1) by the cells of the ROSA KIT WT line (flow cytometry analysis).

Figure 3:
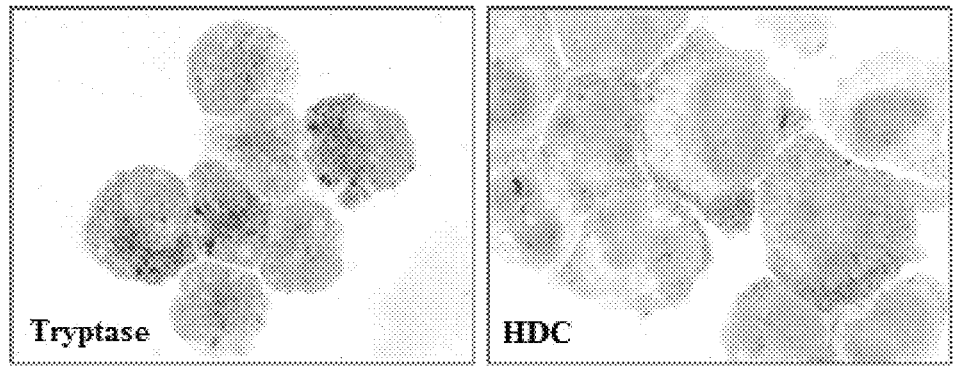

FIG. 3: Demonstration of the tryptase content and HDC content of the cells of the ROSA KIT WT line by the immunocytochemical method on cytospun cells.

Figure 4:
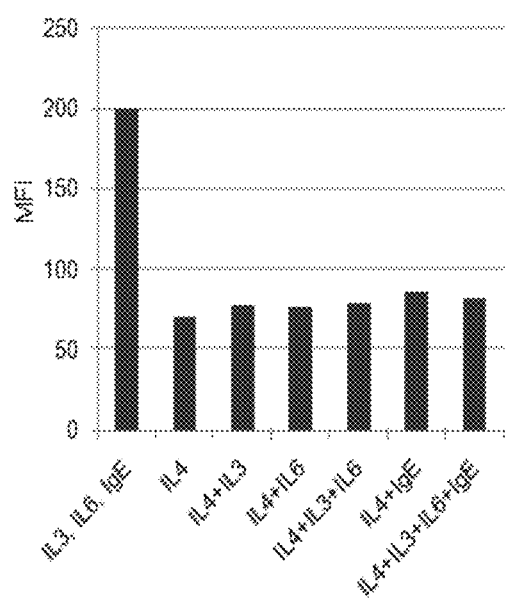
Figure 4:
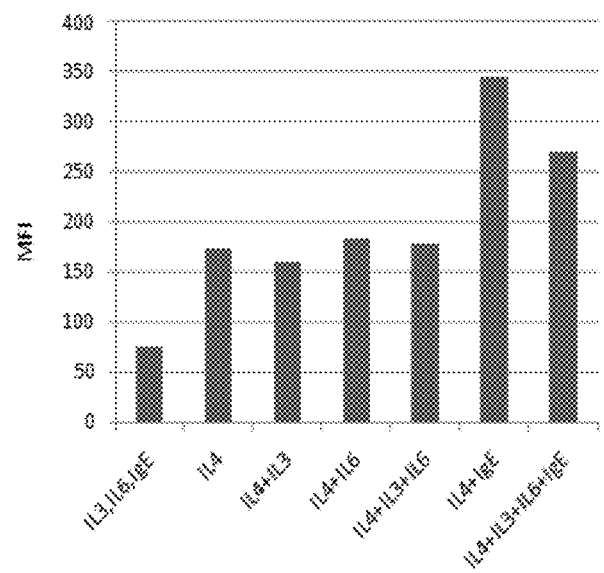

FIG. 4: Flow cytometry study of various compounds, including IL-4, on the expression of KIT and of FcεR1 by the cells of the ROSA KIT WT line.

Figure 5:
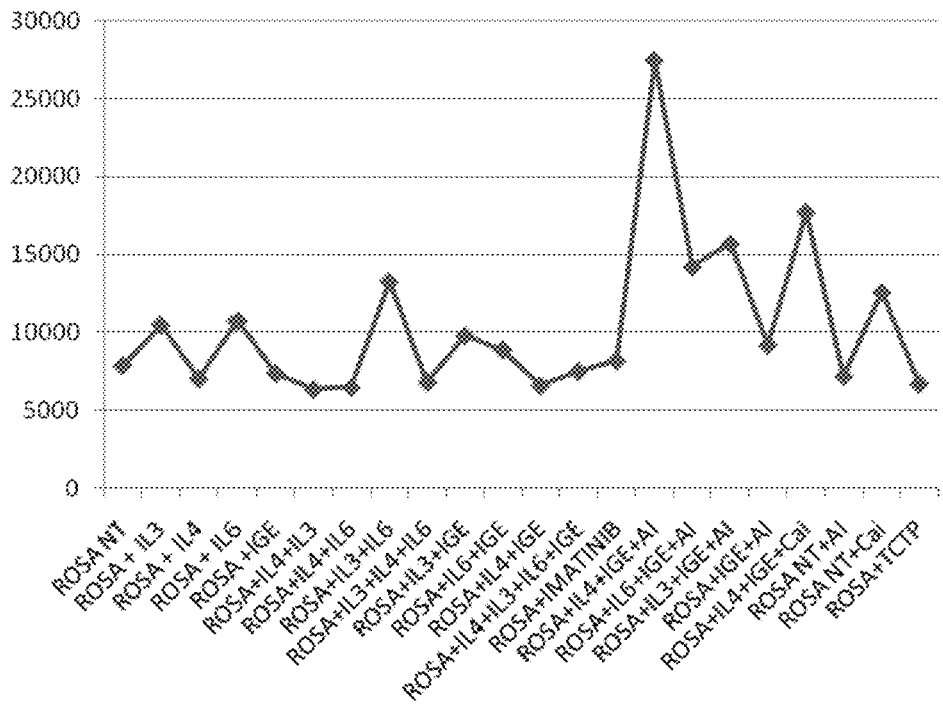

FIG. 5: Flow cytometry study of the effect of various treatments on the expression of membrane CD203c by the cells of the ROSA KIT WT line.

Figure 6:
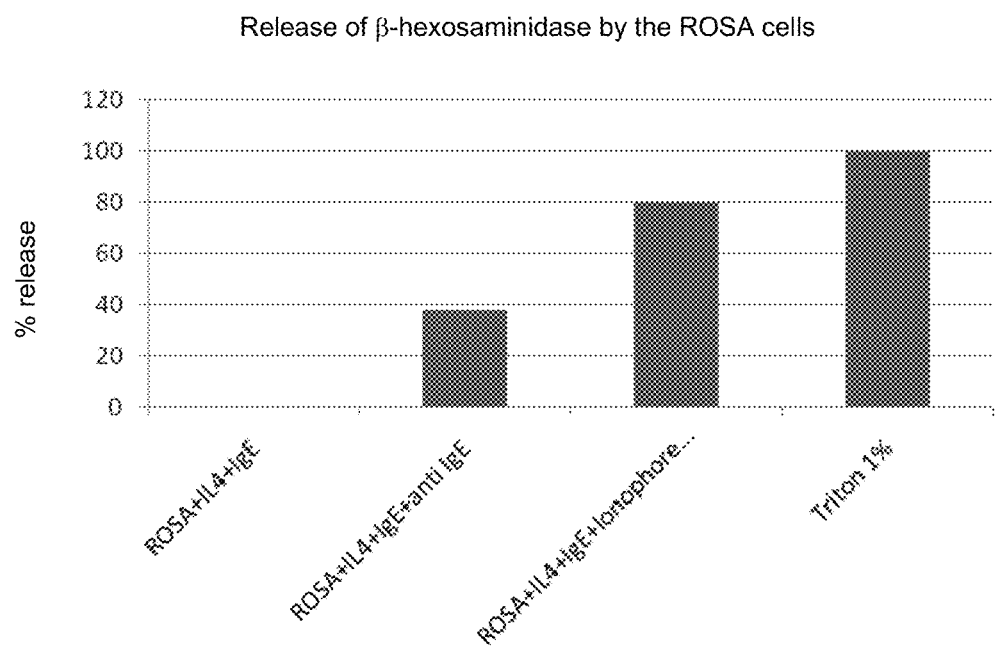

FIG. 6: Measurement by the spectrophotometric method of the β-hexosaminidase activity released by the cells of the ROSA KIT WT line after stimulation thereof.

Figure 7:
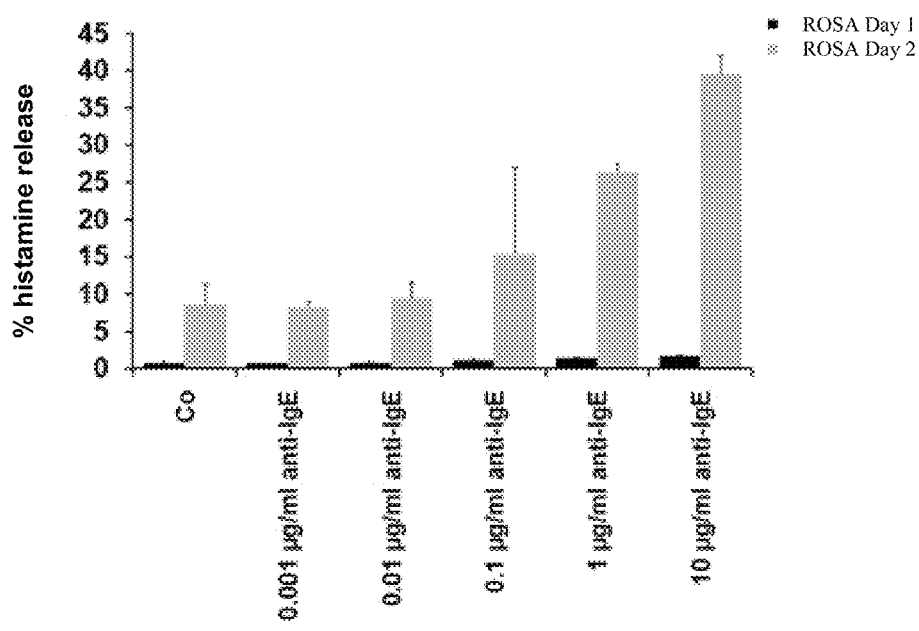

FIG. 7: Measurement of the percentage of histamine released by the cells of the ROSA KIT WT line after stimulation thereof by the IgE-anti-IgE pairing.

Figure 8:
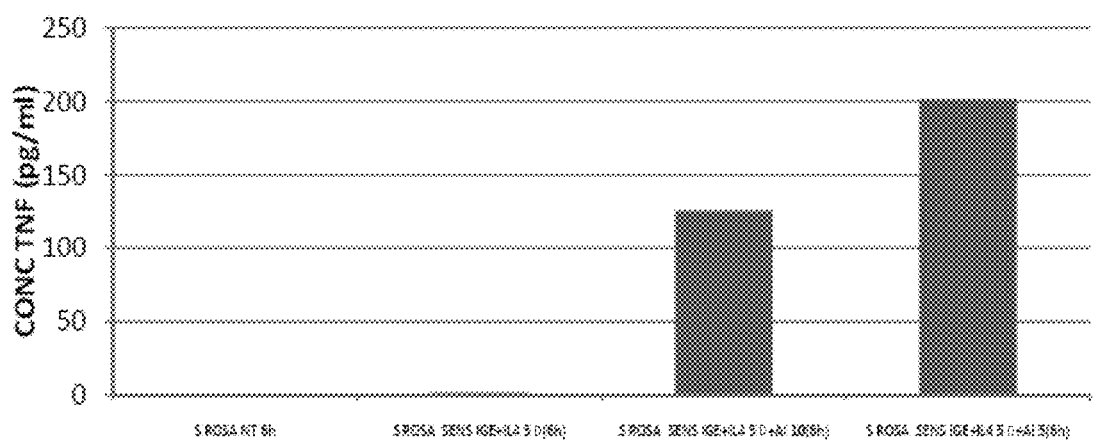

FIG. 8: Measurement of the TNF-α released into the supernatant of the cells of the ROSA KIT WT line after stimulation thereof for 6 hours with the IgE-anti-IgE pairing.

Figure 9:
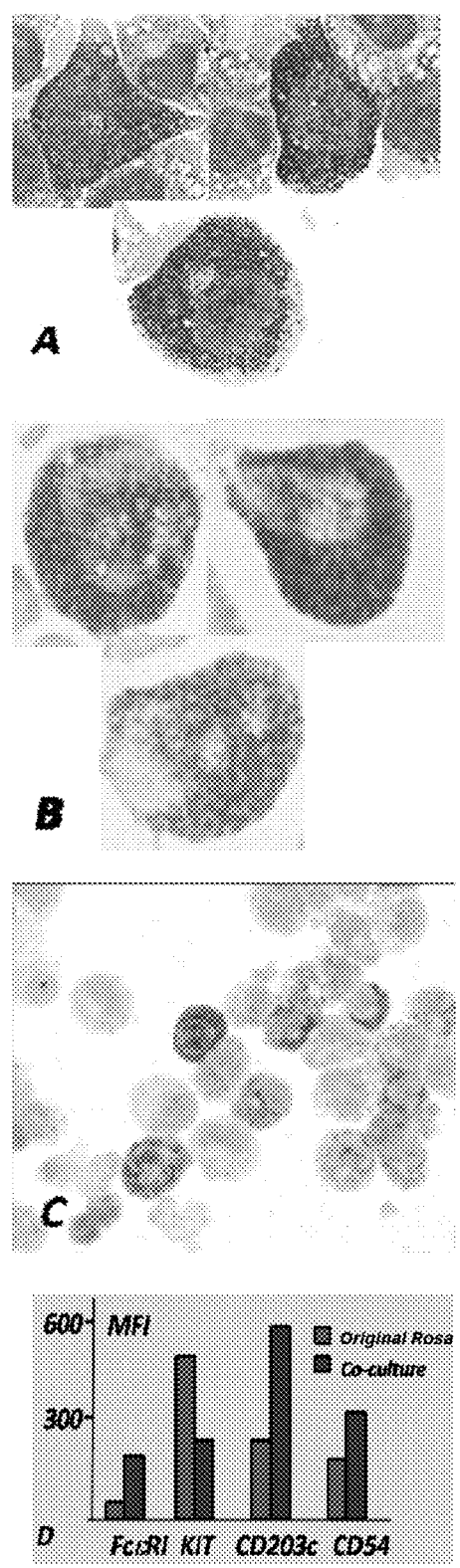

FIG. 9: Morphological and phenotypic appearance of the cells of the ROSA KIT WT line cocultured for more than three months on a sublayer of MS-5 mouse lipoblast cells (A: MGG staining; B: toluidine blue staining; C: immunocytochemical labelling of chymase; D: flow cytometry analysis of various membrane markers).

Figure 10:
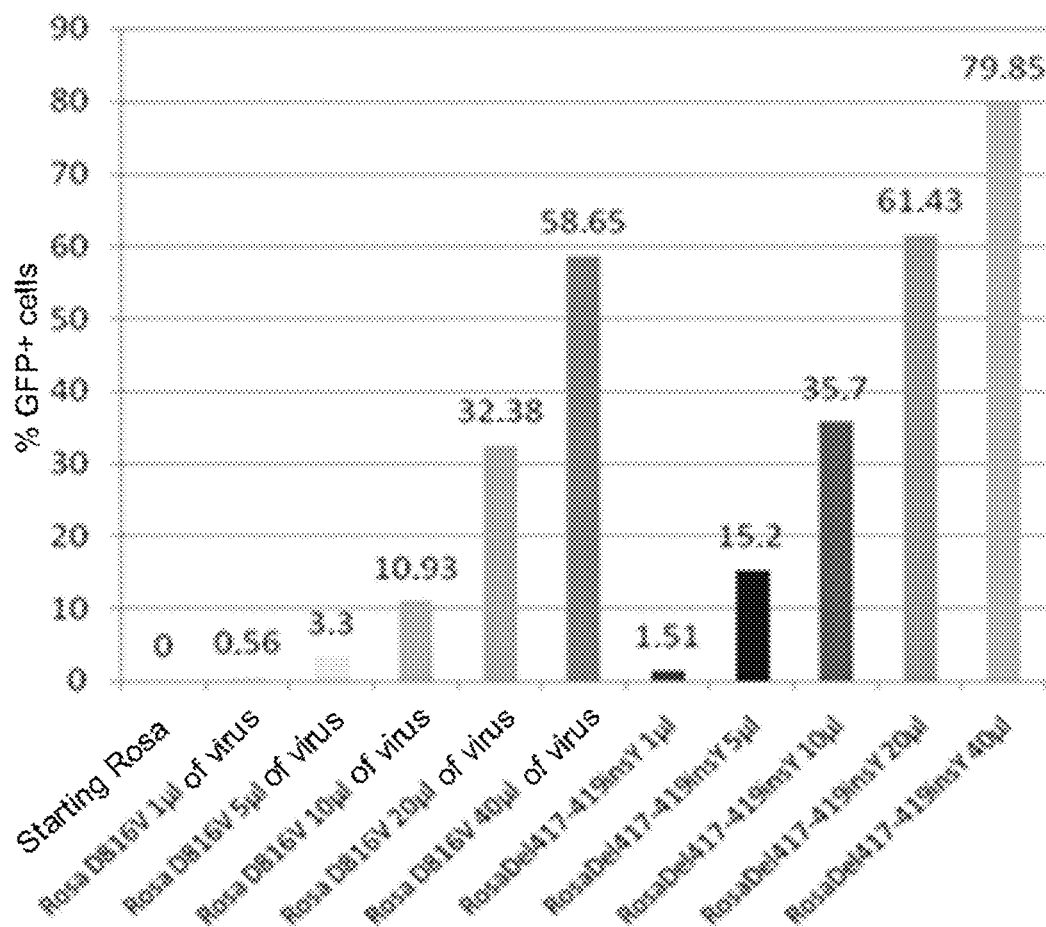

FIG. 10: Measurement of the infection efficiency by flow cytometry (% of cells positive for GFP) four days after contact of the ROSA KIT WT cells with the various lentiviral constructs used at increasing concentrations.

Figure 11:
Figure 11:
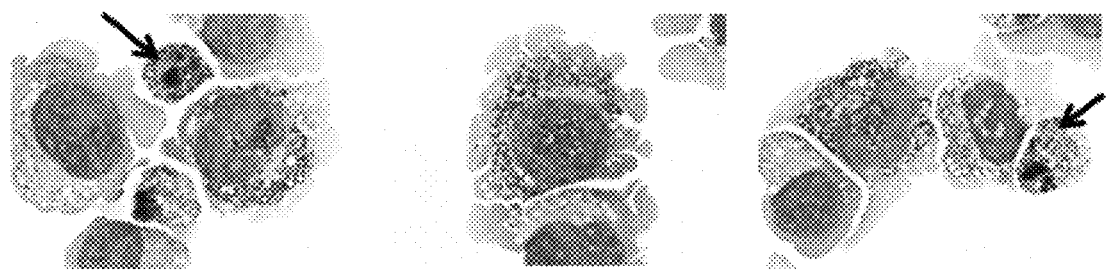

FIG. 11: Morphological appearance of the cells of the ROSA KIT Delta 417-419 insY and KIT D816V lines after MGG staining. Presence of immature cells, without any granulation for the ROSA KIT Delta 417-419 insY line (red arrow), while in the ROSA KIT D816V line, cells undergoing apoptosis are observed, with numerous granules.

Figure 12:
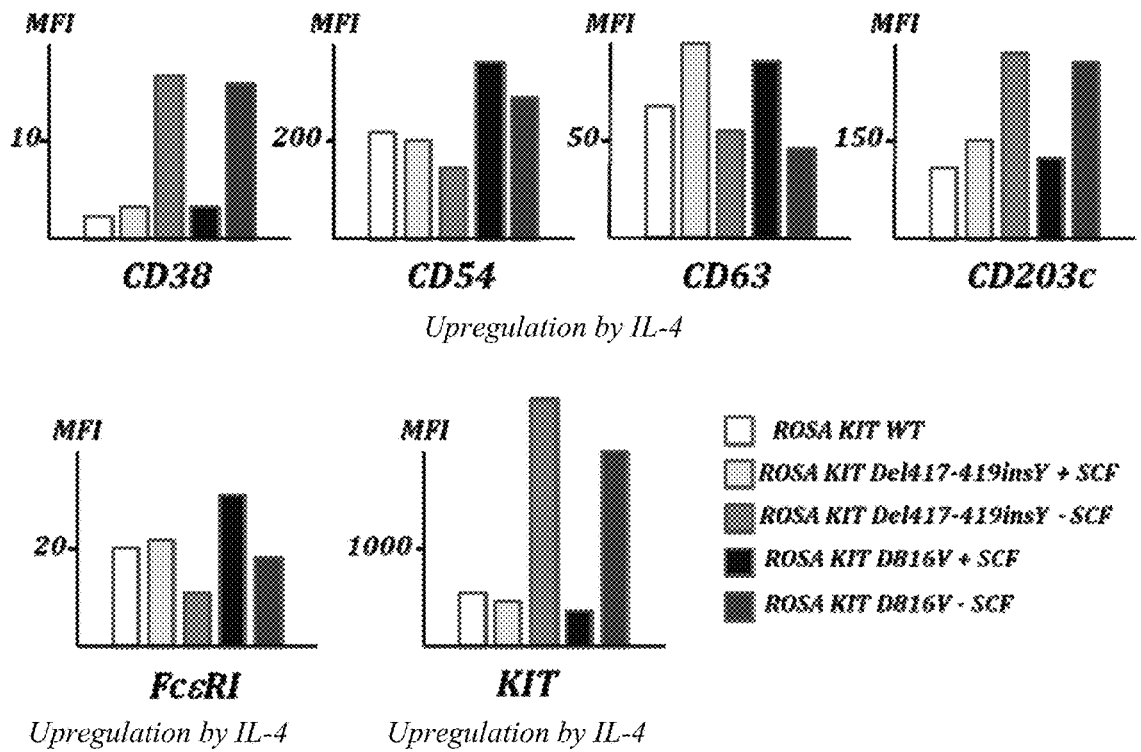

FIG. 12: Flow cytometry study of the expression of certain membrane markers by cells of the ROSA KIT Delta 417-419 insY and KIT D816V lines treated or not treated with SCF (80 ng/ml) and by cells of the ROSA KIT WT line.

Figure 13:
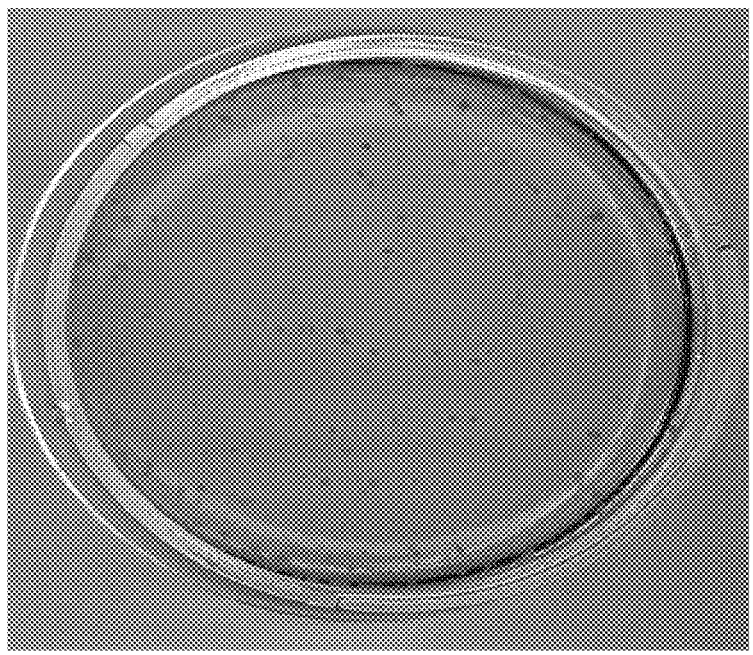

FIG. 13: Example of the appearance of a culture in semi-solid medium (1% methylcellulose) of the cells of the ROSA KIT Delta 417-419 insY line after incubation for 15 days in a Petri dish. The colonies, of variable sizes, are identifiable to the naked eye.

Figure 14:
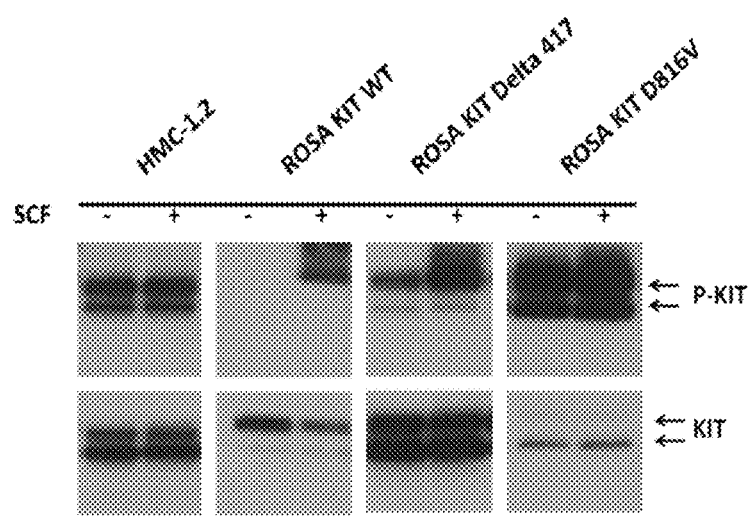

FIG. 14: Demonstration by Western blotting of the spontaneous phosphorylation of KIT in the HMC-1.2, ROSA KIT D816V and ROSA KIT Delta 417-419 insY lines. The cell lysates prepared from the nonstimulated cells or the cells stimulated for 5 minutes with human SCF were subjected to SDS-PAGE and treated with an anti-P KIT Y703 antibody (Cell signalling, ref: 3073S). The membranes were subsequently dehybridized and then rehybridized with an anti-KIT antibody (Santa Cruz Biotechnology, ref: J2709).

Figure 15:
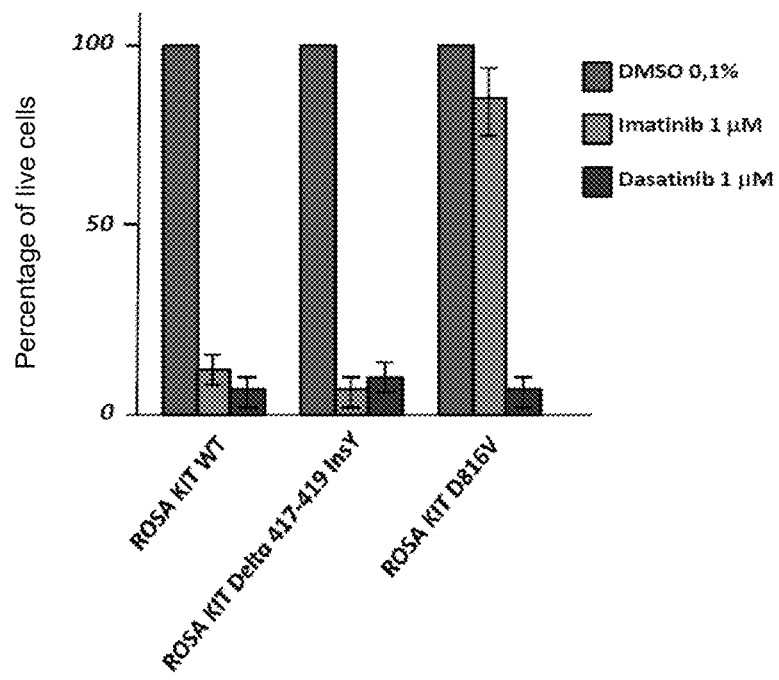

FIG. 15: Demonstration of the effect of tyrosine kinase inhibitors on the proliferation of the ROSA KIT WT, ROSA KIT Delta 417-419 insY and ROSA KIT D816V lines. The values presented are compared with those obtained without inhibitor. The results represent the mean +/− standard deviation of triplicates.

Figure 16:
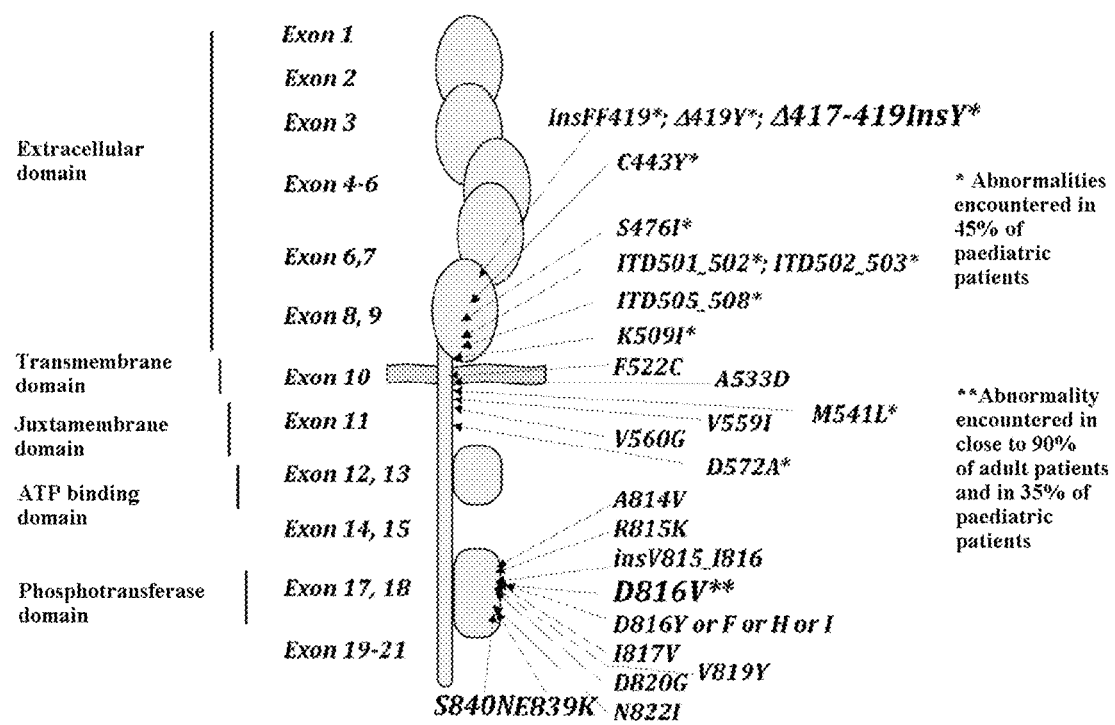

FIG. 16: Structure of the KIT receptor (CD117) and principal abnormalities encountered during mastocytoses.

Figure 17:
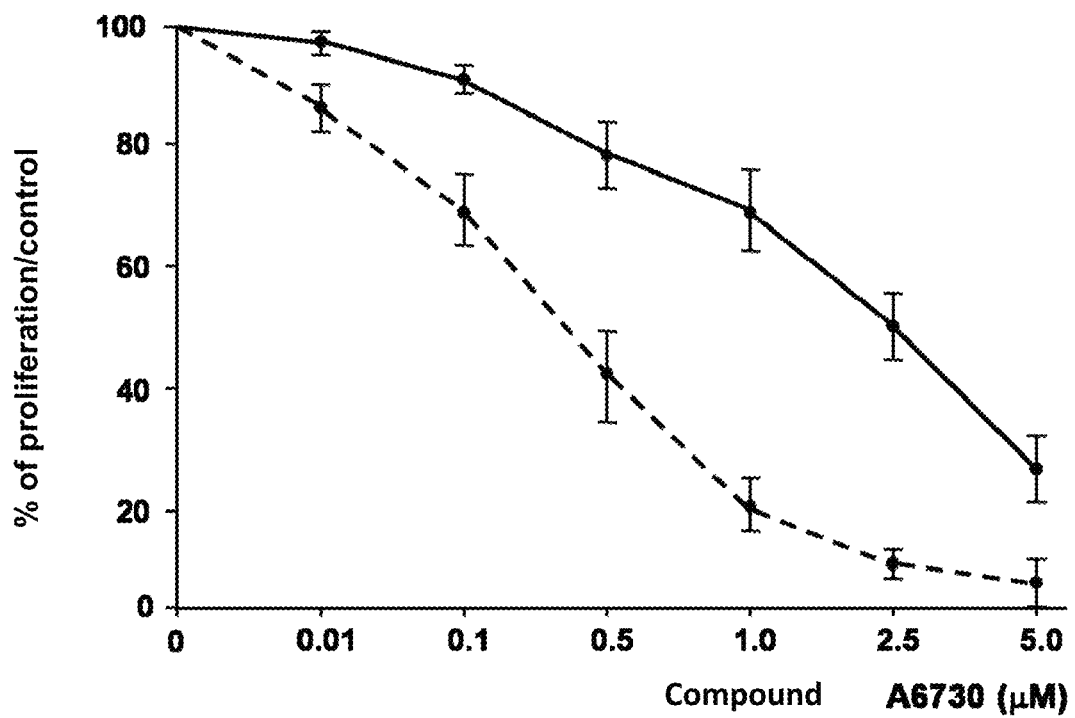

FIG. 17: Effect of the specific inhibition of AKT on the proliferation of the two ROSA cell lines.

The ROSA$^{KIT\ WT}$ (−) or ROSA$^{KIT\ D816V}$ ( - - - ) cells are seeded for 48 hours in the presence of variable concentrations (0.01 to 5 μM) of the powerful and selective inhibitor of AKT1/AKT2, the A6730 compound (diluted in DMSO to a final concentration of 0.1%), or in the presence of DMSO alone (final concentration of 0.1%) in SFM (with rhSCF at 80 ng/ml for the ROSA KIT WT cells but not for the ROSA KIT D816V cells). At the end of this incubation period, 10 μl of MTT (3-(4,5-dimethylthiazol-2-yl)-2,5-diphenyltetrazolium bromide) were added to each well and the cells were incubated for a further 3 hours in an incubator at 37° C. The number of live cells was then measured for each condition by reading the absorbance at 450 nm. The data given in FIG. 17 represent the mean±the standard deviation obtained from 3 independent experiments and are expressed as percentage proliferation for each condition relative to the control (DMSO alone) representing 100% proliferation.

Figure 18:
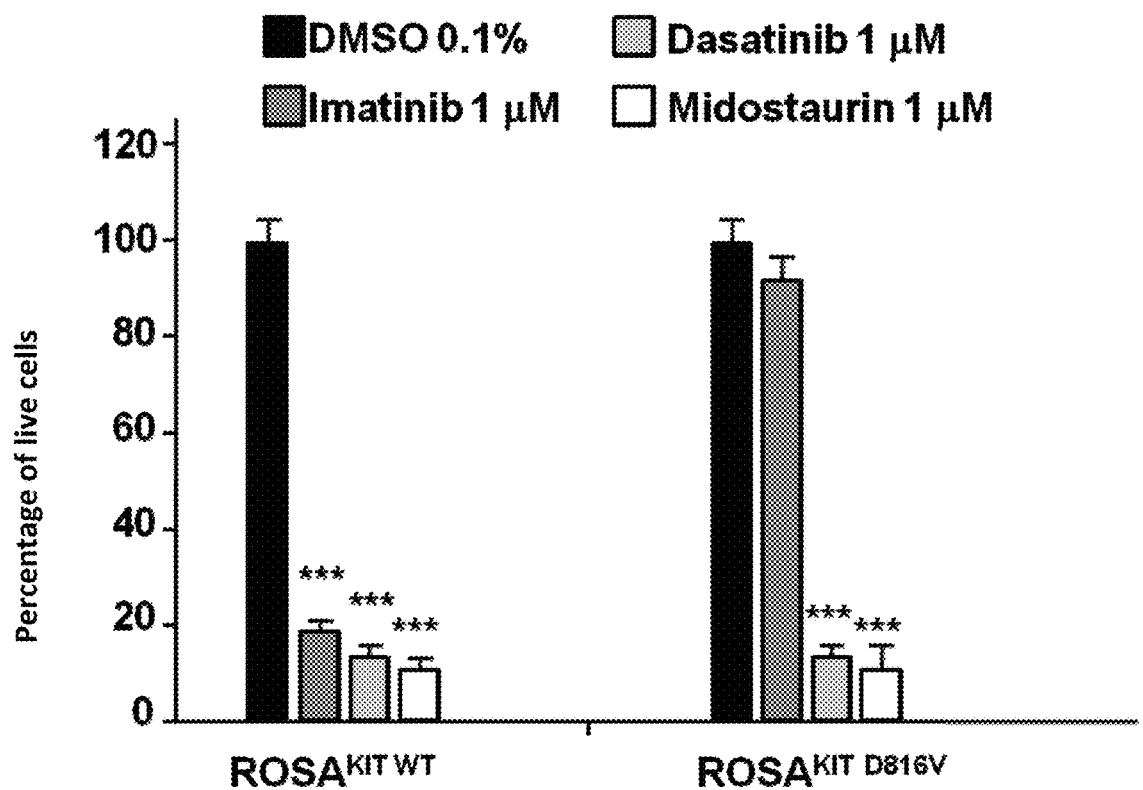

FIG. 18: Effect of three tyrosine kinase inhibitors on the proliferation of the two ROSA cell lines.

The cells were seeded for 48 hours in the presence of imatinib, dasatinib or midostaurin (1 μM, supplied in DMSO at a final concentration of 0.1%) or in the presence of DMSO alone (final concentration 0.1%) in a conventional culture medium (containing human SCF at 80 ng/ml for the ROSA$^{KIT\ WT}$ cells but without SCF for the ROSA$^{KIT\ D816V}$ cells). At the end of this incubation period, 10 μl of MTT (3-(4,5-dimethylthiazol-2-yl)-2,5-diphenyltetrazolium bromide) were added to each well and the cells were incubated for an additional 3 hours in an incubator at 37° C. The number of live cells was then measured for each condition by reading the absorbance at 450 nm. The data given in FIG. 18 represent the mean±the standard deviation obtained from 3 independent experiments. ***: value significantly different from the control (DMSO alone) at p<0.0001.

Figure 19:
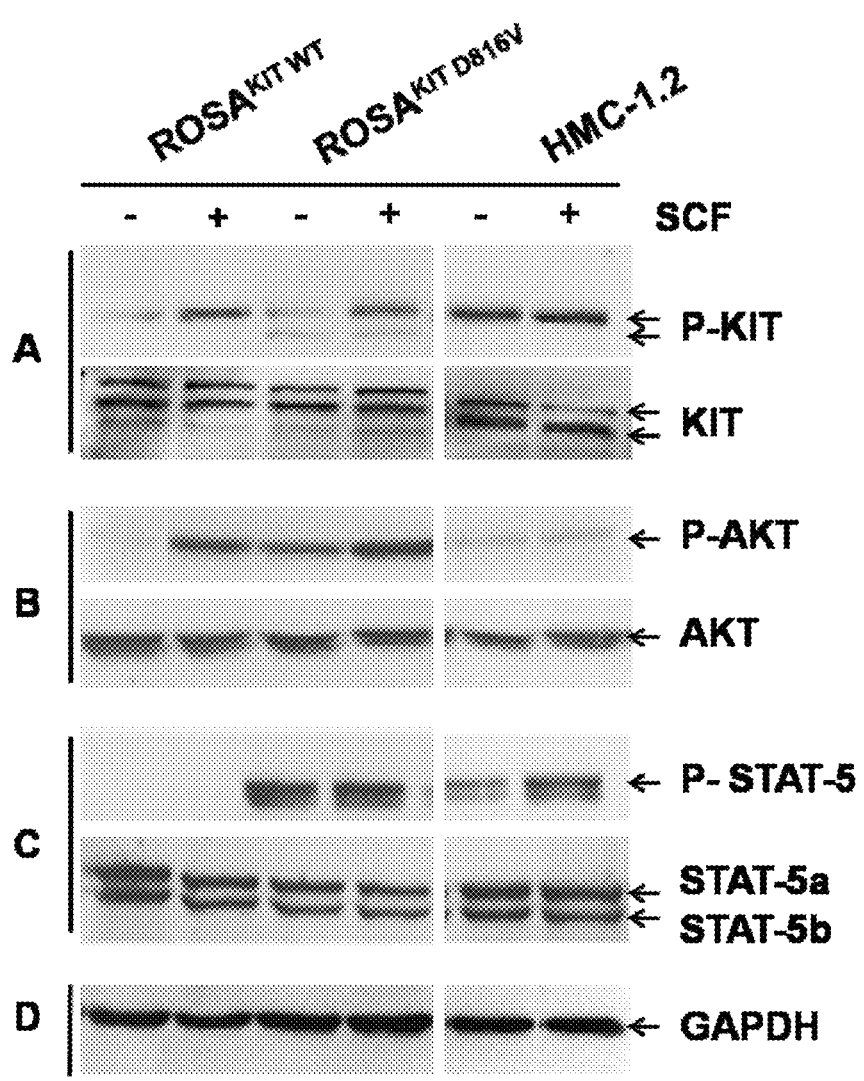

FIG. 19: Demonstration by Western blotting of the spontaneous phosphorylation of KIT, AKT and STAT-5 in the ROSA$^{KIT\ D816V}$ cells.

The cell lysates originating from nonstimulated ROSA cell lines and from the HMC-1.2 cell line or from identical cells stimulated for 10 minutes with human SCF were subjected to SDS-PAGE and treated with an anti-total human KIT or with an anti-P-KIT Y703 (A), with an anti-total human AKT or an anti-P-AKT S473 (B), or with an anti-total human STAT-5 or an anti-P-STAT-5 Y694 (C). D: an anti-human GAPDH was used as a loading control.

EXAMPLES

Example 1: Isolation, Characterization and Maintenance of Pure Populations of Mast Cells from Normal Human Umbilical Cord Blood: the Rosa KIT WT Line 1) Sampling and Culturing of Cells The normal umbilical cord blood sample was collected on lithium heparinate on 9 Sep. 2009. The blood (40 ml) was immediately diluted 50/50 in PBS buffer (Invitrogen) and the mononuclear cells were separated from the other blood components by centrifugation at 700 g for 30 min on a Ficoll gradient (Eurobio). The mononuclear cells, which form a ring at the interface between the Ficoll and the diluted serum, were recovered and washed with PBS buffer. Counting and cell viability were performed using trypan blue (Sigma). The umbilical cord blood haematopoietic progenitors expressing the CD34 surface antigen were then positively selected by immunomagnetic sorting using the MACS system (Milteny). 85×10$^4$ CD34+ cells were thus obtained.

These purified CD34+ cells were then seeded at 5×10$^4$ per ml (17 ml total) in Iscove's Modified Dulbecco's Medium (IMDM)-Glutamax® (Invitrogen) supplemented with penicillin/streptomycin 100 U/ml (P/S) (Invitrogen), 1% of sodium pyruvate (Invitrogen), 1% of vitamins (Invitrogen), 1% of glutamine (Invitrogen), 2% of non-essential amino acids (Invitrogen), 1% of a commercial solution of insulin-transferrin-sodium selenite (Invitrogen) and 0.3% of bovine albumin (BSA) (PAA).

Various cytokines were added to the cell suspension in order to direct the differentiation towards mast cells: SCF at 80 ng/ml (R&D), IL-6 at 50 ng/ml (R&D) and IL-3 at 1 ng/ml (R&D). The IL-3 and the IL-6 were added only during the first week of culture. The cells were then placed in an incubator at 37° C., under a humid atmosphere containing 5% $CO_2$.

The medium was renewed once or twice a week and the cells were maintained at $7 \times 10^5$ per ml for 8 to 12 weeks until a pure population of mast cells was obtained.

Unlike the usual behaviour of this type of culture, the umbilical cord cells of 9 Sep. 2009 called "ROSA KIT WT" have continued to proliferate in the same culture medium containing 80 ng/ml of human SCF up until now with a doubling time of 48 hours. The cells have therefore been maintained in culture since the beginning by 1/3 or 1/4 dilution in new culture medium every 3 or 4 days. The cells can be repeatedly frozen and thawed using the conventional freezing methods (decomplemented foetal calf serum (FCS) (PAA) containing 10% of DMSO (Sigma)).

2) Characterization of the Cells

The identification of the ROSA KIT WT line as a mast cell line was carried out by toluidine blue staining and May-Grünwald Giemsa (MGG) staining, transmission electron microscopy study and demonstration of intracellular tryptase and of intracellular histidine decarboxylase (HDC).

After MGG staining (FIG. 1), the cells of the ROSA KIT WT line appeared to be rounded with a very high nuclear-cytoplasmic ratio. In the cytoplasm, which is basophilic, the presence of numerous dark violet-coloured granulations is noted. The number and the size of the granulations varies: they are small and sparse in the cells considered to be immature; they are numerous and large in the cells considered to be mature. Their metachromasia was revealed using the toluidine blue staining technique.

The morphological characterization was completed by electron microscopy observation (FIG. 1). The mast cells of the ROSA KIT WT line observed are cells which have a large nucleus, with loose chromatin suggesting that they are quite young cells. One to two nucleoli are observed in the nucleus. The cytoplasm contains ribosomes, numerous mitochondria and numerous granulations. These granulations are of the same type as those described in human mast cells in primary culture.

Demonstration of the KIT Receptor and of the IgE Receptor

Direct labelling at various culture times was carried out by flow cytometry on the cells of the ROSA KIT WT line in culture with an antibody directed against the alpha (a) chain of the high-affinity IgE receptor coupled to the FITC fluorochrome (Fluorescein) (Biolegend) or with the anti-human KIT (CD117) antibody coupled to APC (Biolegend).

1 ml of cells in culture at approximately $10^6$ cells/ml is used for each tube.

The cells are centrifuged in order to remove the culture medium.

The pellets are taken up in 100 µl of PBS+1% FCS, and incubated for 45 min at +4° C. in the presence of anti-human IgE antibody coupled to FITC (20 µl/1 million cells), or in the presence of anti-human KIT antibody coupled to APC (20 µl/1 million cells).

Two rinses are carried out in 3 ml of PBS, 0.1% FCS, and then the tubes are centrifuged.

The pellets are collected in 300 µl of PBS, 0.1% FCS.

The reading is carried out by flow cytometry (BD FACSCalibur).

As shown in FIG. 2, it appears that the cells of the ROSA KIT WT line that are analysed significantly express the IgE receptor and also the KIT receptor.

Demonstration of the Expression of Tryptase and of Histidine Decarboxylase (HDC)

The presence of intracellular tryptase and of intracellular histidine decarboxylase (HDC) was demonstrated in the cells of the ROSA KIT WT line by immunohistochemical methods on cytospun cells.

The tryptase and the HDC are detected using a monoclonal anti-tryptase antibody (Dako) or an anti-HDC antibody (Santa Cruz).

Indirect labelling was carried out on slides after cytospinning of the cells for 10 minutes at 500 revolutions per minute.

After cytospinning, the cells are fixed with acetone for 8 min.

They are then rinsed twice in TBS and air-dried for 20 min, then incubated with the first antibody (anti-tryptase diluted to $1/250^{th}$ in TBS-1% BSA, or anti-HDC diluted to 1/250) for 1 hour at ambient temperature in a humid chamber. After three rinses in TBS (3×5 min), the cells are incubated with the second antibody (biotinylated goat anti-mouse IgG (Dako)) for 30 min at ambient temperature in a humid chamber, and then rinsed three times (5 min each time) in TBS.

The cells are then incubated with the third antibody (Streptavidin AP (Dako)) for 30 min at ambient temperature in a humid chamber. After three rinses in TBS (3×5 min), 100 µl of New Fuchsin are applied to each slide for 10 minutes. Rinsing is again carried out three times (5 min each time) in TBS, followed by incubation at ambient temperature for 3 min with haematoxylin. Finally, the slides are rinsed for 5 min with $H_2O$ and are mounted in Aquatex.

The reading is carried out under an optical microscope.

Positive labelling of the two enzymes in virtually all the ROSA cells is observed (FIG. 3). The strong tryptase positivity confirms the mast cell nature of the cells of the ROSA KIT WT line.

3) Effect of the Treatment with IL-4 or with Other Molecules of the Cells of the ROSA KIT WT Line on FcɛRI and KIT Expression Since it has been shown in the literature that interleukin-4 (IL-4) induces a decrease in KIT expression and an increase in FcɛR1 expression by normal human mast cells, the inventors wanted to verify whether this phenomenon could also be observed on the ROSA KIT WT line. For this, they used the following technique:

10 ml of cells in culture at approximately $2 \times 10^5$ cell/ml are used for each tube.

The cells are centrifuged and the pellet is taken up in 10 ml of new culture medium and then the cells are treated with IL-4 (20 ng/ml) (R&D) for 5 days.

The cells are centrifuged in order to remove the culture medium.

The pellets are taken up in 100 µl of PBS+1% FCS, and incubated for 45 min at +4° C. in the presence of anti-human IgE antibody coupled to FITC (20 µl/1 million cells (Merck Bioscience)), or in the presence of anti-human KIT antibody coupled to APC (20 µl/1 million cells) (Biolegend).

Two rinses are carried out in 3 ml of PBS, 0.1% FCS, and then the tubes are centrifuged.

The pellets are collected in 300 µl of PBS, 0.1% FCS.

The reading is carried out by FACS (BD FACSCalibur).

The results obtained are given in FIG. 4 and show that this treatment with IL-4 indeed induces a decrease in KIT expression and an increase in that of the high-affinity IgE receptor on the ROSA KIT WT cells. These cells therefore indeed behave like normal human mast cells from this point of view.

4) Demonstration of the Activation of the Cells of the ROSA KIT WT Line by the IgE-Anti-IgE Pairing In order to know whether the cells of the ROSA KIT WT line can be activated by the IgE-anti-IgE antibody coupling, resulting in degranulation with immediate release of histamine and of β-hexosaminidase associated with a significant increase in membrane CD203c expression and with delayed release of TNF-alpha, cells are treated with IL-4 (20 ng/ml) and IgE (2 µg/ml) (Merck Bioscience) for 5 days and then stimulated with anti-IgE (5 or 10 µg/ml) (Biovalley) or with the calcium ionophore (Cai) (Sigma) (1 µmol/l) for 1 or 6 hours. The 1 hour supernatant and also the pellet are used to assay the histamine and to measure the expression of CD203c at the cell surface, while the TNF-alpha is measured by a specific ELISA method in the supernatant of the cells after 6 hours of stimulation.

a) Increase in Membrane CD203c Expression on the Cells of the ROSA KIT WT Line Treated with IL-4 and IgE and then Stimulated with Anti-IgE One ml of cells treated with IL-4 (20 ng/ml) and IgE (2 µg/ml) for 5 days are washed twice with 3 ml of PBS and then again placed in culture medium at a concentration of $1 \times 10^6$ cells/ml. These cells are then stimulated with anti-IgE (5 or 10 µg/ml) or with the calcium ionophore (Cai) (1 µmol/l) for 1 hour. The cells are washed with PBS and put back into 100 µl of PBS, 1% FCS in the presence of an antibody directed against human CD203c, coupled to phycoerythrin (PE) (20 µl/1 million cells) (Biolegend).

The results, presented in FIG. 5, show a clear increase in CD203c expression when these cells are treated with IL-4+IgE and stimulated with anti-IgE. This increase is also observed when these cells are treated with the calcium ionophore.

b) Release of β-Hexosaminidase into the Supernatant of the Cells of the ROSA KIT WT Line after Activation The activation of the cells of the ROSA KIT WT line was also measured by determining the released β-hexosaminidase activity. ROSA cells treated with IL-4 (20 ng/ml) and IgE (2 µg/ml) are subsequently activated for 1 hour at 37° C. in the presence of 5% $CO_2$, with the anti-IgE antibody (5 µg/ml) or with the calcium ionophore (Cai) (1 µmol/l).

The cells are then centrifuged and the supernatants are recovered and frozen at −80° C. until the time of the assay. The cells are then lysed. The β-hexosaminidase activity is measured in the supernatant and also in the cell pellet as described by Schwartz and Austen, J Invest Dermatol., 74, 349-353, 1980.

The hydrolysis of p-nitrophenyl-2-acetamido-2-deoxy-β-D-glucopyranoside (or 4-nitrophenyl-N-acetyl-β-D-glucosaminide) by β-hexosaminidase leads to the release of a chromophore product: p-nitrophenol. The latter is measured by spectrophotometry at 405 nm.

50 µl of p-nitrophenyl-2-acetamido-2-deoxy-β-D-glucopyranoside (Sigma) are added to 5 µl of supernatant
  Incubation for 2 hours at 37° C. with stirring.
  Addition of 150 µl of stop solution (7.5 g of glycine in 500 ml of $H_2O$, pH=10.7). Reading at 405 nm.

The results obtained and presented in FIG. 6 show that the stimulation of the cells of the ROSA KIT WT line by the IgE-anti-IgE pairing leads to an induction of β-hexosaminidase release which can range up to 38% of the total enzyme content of the cells. As expected, the calcium ionophore, a non-specific stimulant, induces a β-hexosaminidase release which can range up to 80% of the total enzyme content of the cells, which is in accordance with the data from the literature.

c) Measurement of the Histamine Release by the Cells of the ROSA KIT WT Line after their Stimulation 1) Cell Preparation:

50,000 cells treated with IL-4 (20 ng/ml) and IgE (2 µg/ml) for 1 or 4 days were activated for 30 minutes at 37° C. in the presence of 5% $CO_2$ using various concentrations of the anti-IgE antibody. The supernatants and the pellets are recovered and frozen at −80° C. until the time of the histamine assay.

2) Histamine Assay:

The histamine assay was carried out in the supernatants and the pellets using a radio-immunology assay kit (histamine radioimmunoassay (RIA); Immunotech, Marseille, France) in accordance with the supplier's indications (Morel and Delaage, J Allergy Clin Immunol. 1988 October, 82(4): 646-54; Valent et al., Proc Natl Acad Sci USA. 1989 July, 86(14):5542-6).

The net percentage of histamine release is calculated using the following formula:

% release=$S$–$S$ control×100/($S$+$P$)–$S$ control in which:
S=histamine in the supernatant, and
P=histamine in the pellet.

The results obtained (FIG. 7) show that there is a dose-dependent increase (as a function of the concentration of anti-IgE added) in histamine release by the cells of the ROSA KIT WT line when they are stimulated with the IgE-anti-IgE pairing. This release is all the more significant if the cells have been pre-sensitized with IL-4 and IgEs, preferably for at least 4 days. The maximum histamine release obtained, around 40% of the total histamine content of the cells, is absolutely comparable to the beta-hexosaminidase release by the same cells stimulated under the same conditions (FIG. 6).

d) Assays of the TNF-Alpha Released into the Supernatant of the Cells of the ROSA KIT WT Line after their Stimulation Using a specific ELISA kit (Enzyme Linked Immunosorbent Assay, R&D), the late release of TNF-alpha by the ROSA cells treated with IL-4 (20 ng/ml) and IgE (2 µg/ml), and subsequently activated for 6 hours at 37° C., in the presence of 5% $CO_2$, with various concentrations of the anti-IgE antibody (5 or 10 µg/ml) or with the calcium ionophore (Cai) (1 µmol/l), was quantified.

The cells are subsequently centrifuged and the supernatants are recovered and frozen at −80° C. until the time of the TNF-alpha assay.

The results obtained and presented in FIG. 8 show that there is a dose-dependent increase in TNF-alpha release by the ROSA KIT WT cells after stimulation thereof with the IgE-anti-IgE pairing.

5) Demonstration of the Ability of the Cells of the ROSA KIT WT Line to Terminally Mature after Coculture on a Sublayer of MS-5 Cells The cells of the ROSA KIT WT line have a relatively immature human mast cell phenotype (chymase negativity, relatively low metachromasia). It had previously been demonstrated that the culturing of human CD34+ haematopoietic progenitors on a sublayer of mouse lipoblast cells (MS-5 line) enables the terminal mast cell differentiation of these progenitors (Arock et al. Ann N Y Acad Sci. 1994 May 28, 725: 59-68). Cells of the ROSA KIT WT line were therefore grown on a sublayer of MS-5 cells at confluence, for more than 3 months, the culture medium being 50% renewed every 3 or 4 days. After this coculturing time, the non-adherent cells of the coculture were analysed with respect to their morphological appearance after MGG staining (FIG. 9A), their metachromasia with respect to toluidine blue (FIG. 9B), their chymase content (immunocytochemistry) (FIG. 9C) and the expression of various surface markers, including KIT, FcεR1, CD54 and CD203c (FIG. 9D). The analysis of these results shows that the cells of the ROSA KIT WT line can acquire a totally mature human mast cell (MCTC) phenotype after this coculturing time. Indeed, the cells exhibit a considerable increase in the number of granulations in their cytoplasm (MGG staining) which are metachromatic (toluidine blue staining). In addition, the cocultured cells express chymase and are more strongly positive than the non-cocultured cells in terms of the expression of FcεR1, CD54 and CD203c, all three of which are maturation markers.

Example 2: Obtaining of Immortalized Lines of Human Mast Cells Transfected with a Kit Receptor of Abnormal Structure: The Rosa Kit D816V AND ROSA KIT Delta 417-419 insY LINES With the aim of obtaining and characterizing SCF-independent subclones of the starting ROSA line, the cells were transfected with lentiviral vectors providing a construct encoding D816V-mutated KIT or the mutated KIT Delta 417-419 insY. These two acquired structural abnormalities of the KIT receptor are frequently encountered, respectively, during systematic mastocytoses in adults (KIT D816V; Féger et al. Int Arch Allergy Immunol. 2002 February, 127(2): 110-4) or during cutaneous mastocytoses in children (KIT Delta 417-419 insY; Bodemer et al. J Invest Dermatol 2010, 30(3): 804-15). Furthermore, it has been shown that the D816V mutation is capable of inducing systematic mastocytosis in transgenic mice (Zappulla et al. J Exp Med. 2005 Dec. 19, 202(12): 1635-41).

1) Transfection Procedure Used a) Site-Directed Mutagenesis and Plasmid Vectors

In order to prepare the corresponding constructs, the cDNA encoding the short isoform of human wild-type KIT was excised from the pBS-hkitWT vector by Sal I-Acc65 digestion. The cDNA fragment was subcloned into the pENTR1A vector (Invitrogen, France). The two KIT mutations (D816V-mutated KIT or the mutated KIT Delta 417-419 insY) were introduced into the pENTR1A-hkitWT vector encoding the green fluorescent protein (GFP) using a QuickChange™ site-directed mutagenesis KIT (Stratagene, The Netherlands) in accordance with the manufacturer's instructions. For the KIT D816V mutant, codon 816 of WT KIT (GAC) was replaced with the GTC codon. For the KIT Delta 417-419 insY mutant, the WT KIT codons 417/418/419 (ACTTACGAC) were replaced with the TAC codon.

b) Bacterial Transformation for Amplification and Purification of the Plasmid DNAs Encoding the Mutated Forms of KIT 5-10 µl of plasmid are added per tube of bacteria (XL10-Gold® Ultracompetent Cells #200314, Stratagene) and the bacteria are subjected to a heat shock (30 minutes on ice, then 30-40 seconds at 42° C. and then 2 minutes on ice). 1 ml of medium (SOC) without ampicillin is then added per tube and incubation is carried out for 30 minutes at 37° C. with shaking. The transformed bacteria are then plated out using sterile beads on a Petri dish containing LB medium+ampicillin (2 Petri dishes for each plasmid encoding either KIT D816V or KITD 417-419 insY). These Petri dishes are then incubated at 37° C. overnight. After this incubation, one bacteria colony is picked for each plasmid and is suspended in 200 ml of LB medium+ampicillin which is incubated at 37° C. overnight. The preparation is then centrifuged for 15 minutes at 4° C. at 8000 g, the supernatant is removed, and 12 ml of RES buffer containing RNAse (NucleoBond® AX), followed by 12 ml of LYS lysis buffer, are added to the pellet and mixing is carefully carried out by inverting the tube 8 times. The mixture is incubated for 5 minutes at ambient temperature. The lysate is then passed through the NucleoBond® Xtra column, which is allowed to empty by gravity. The column is rinsed with 15 ml of EQU buffer and then the filter is discarded by turning the column upside down. The column is washed with 25 ml of WASH buffer and the plasmid DNA is eluted with the ELU elution buffer. The elution buffer with the plasmid DNA is collected in a 50 ml tube and the eluted plasmid DNA is precipitated by adding isopropanol at ambient temperature for 2 minutes. Centrifugation is carried out at 15,000 g for 30 minutes at ambient temperature, the supernatant is carefully removed and 70% ethanol at ambient temperature is added to the pellets, centrifugation is carried out at 15,000 g for 5 minutes at ambient temperature, and then the ethanol is carefully and completely removed with a pipette and the pellet is left to dry at ambient temperature. The pellet is subsequently dissolved in an appropriate volume of TE buffer and the yield and the purity of the plasmid DNA are determined by UV spectrophotometry (NanoDrop). The integrity of the plasmid is confirmed by agarose electrophoresis.

c) Production of Lentiviral Stocks

In order to produce lentiviral stocks, 293T cells (human epithelium) were used and the lentiviral infection was carried out by means of the calcium phosphate method according to the method described in, Zufferey et al. J Virol. 1998 December, 72(12): 9873-9880.

To do this, the 293T cells ($5 \times 10^6$ cells) were seeded in 75 cm$^2$ culture flasks (T-75) and infected the following day with 8 µg of Gag-pol, 3 µg of a plasmid encoding the viral envelope of the vesicular stomatitis virus G (VSV-G) and 15 µg of the plasmid DNA encoding either KIT D816V or KIT Delta 417-418 419 inserY. Twenty-four hours later, the culture supernatant is filtered with a 0.45 µm filter (low protein-binding Durapore; Millipore). The filtered supernatant was then ultracentrifuged at 20,000 rpm for 2 h under vacuum. After centrifugation, the supernatant was removed and the pellet (virus) was taken up in 200 µl of PBS. These viral stocks were aliquoted into tubes and frozen at −80° C. until their use.

d) Infection of ROSA KIT WT Cells with the Lentiviral Vectors

For the infection of the ROSA KIT WT cells, the cells ($10^6$) were incubated for 1 hour in 1 ml of medium containing SCF (80 ng/ml) and 8 µg/ml of polybrene (hexadimethrine bromide). The cells were then incubated for 3 hours with variable amounts of infectious particles, centrifuged, and diluted in new medium containing SCF. The infection efficiency was measured by flow cytometry (detection of the green fluorescence of GFP) 4 days later (FIG. 10).

The cells were then subcultured in the same medium for 3 weeks, and the GFP-positive infected cells were then selected by cell sorting by flow cytometry and immediately grown in an SCF-free medium. They have, since then, been maintained by regular dilution (every 3 or 4 days) in new SCF-free medium.

This made it possible to establish two new SCF-independent lines, ROSA KIT D816V and ROSA KIT Delta 417-419 insY, the principal characteristics of which are described below.

These two lines can be used for high-throughput screening for molecules for anti-proliferative purposes, directed either against the mutated KIT molecule, or against one or another of the intracellular molecules involved in the mutated KIT signal transduction.

2) Principal Characteristics of the ROSA KIT D816V and KIT Delta 417-419 insY Lines These two lines can be easily frozen by conventional freezing techniques (see above). The two lines have a different doubling time, about 48 hours for the ROSA KIT Delta 417-419 insY line and about 72 hours for the ROSA KIT D816V line. Their morphological appearance is also different. Specifically, while, after MGG staining, the cells of the ROSA KIT Delta 417-419 insY line appear to be homogeneous and relatively immature with few granules, the cells of the ROSA KIT D816V line appear to be more mature and more granular (FIG. 11). This is in agreement with the data from the literature showing that the introduction of the KIT D816V mutation into a mouse haematopoietic precursor line induces the appearance of mast cell differentiation characteristics (Mayerhofer et al. J Immunol. 2008 Apr. 15, 180(8): 5466-76).

Moreover, the expression of certain membrane markers present on the cells of the ROSA KIT Delta 417-419 insY and KIT D816V lines, optionally present in the presence of SCF, was studied by flow cytometry, this expression being compared with that of the cells of the ROSA KIT WT line. The results obtained (presented in FIG. 12) were the following:

the cells of the ROSA KIT Delta 417-419 insY and KIT D816V lines spontaneously express (in the absence of SCF) more CD38, CD203c and KIT than the cells of the ROSA KIT WT line, this increase in expression being completely abolished in the presence of SCF, the cells of the KIT D816V line express more CD54 than the cells of the other two lines, whether in the absence or in the presence of SCF, the cells of the KIT D816V line express more FcεR1 than the cells of the other two lines in the absence of SCF, this phenomenon being abolished by adding SCF, the cells of the ROSA KIT Delta 417-419 insY and KIT D816V lines express, in the presence of SCF, more CD63 than the cells of the ROSA KIT WT line, this increase in expression being completely abolished in the absence of SCF, the expression of CD53 and of FcεR1 is increased in the 3 lines by treatment with IL-4 (20 ng/ml), and the expression of KIT is decreased in the three lines by treatment with IL-4 (20 ng/ml).

Furthermore, the inventors have studied the cloning capacity in semi-solid medium (methylcellulose) of the two lines, ROSA KIT Delta 417-419 insY and KIT D816V, in the absence of SCF, comparing it with that of the cells of the ROSA KIT WT line (in the presence of SCF at 80 ng/ml). To do this, the cultures were seeded in a proportion of 5000 per Petri dish containing 1 ml of culture medium supplemented with 1% of methylcellulose (final concentration) and incubated at 37° C. in a humid atmosphere containing 5% $CO_2$ in air. The colonies were counted after 28 days of incubation for ROSA KIT WT and 15 days of incubation for ROSA KIT Delta 417-419 insY and KIT D816V. An example of culturing in semi-solid medium is shown in FIG. 12 and the results obtained are presented in Table I.

TABLE I

Study of the clonogenicity of the cells of the ROSA KIT WT, KIT Delta 417-419 insY and KIT D816V lines in semi-solid medium (1% methylcellulose)

| Line | Number of colonies dish 1 | Number of colonies dish 2 | Number of colonies dish 3 | Mean | Percentage of clonogenic cells |
|---|---|---|---|---|---|
| ROSA KIT WT | 238 | 408 | 372 | 333 | 6.8% |
| ROSA KIT Delta 417-419 insY | 173 | 438 | 445 | 352 | 7.04% |
| ROSA KIT D816V | 203 | 117 | 292 | 204 | 4.08% |

The results of these experiments show that the cells of the ROSA KIT WT and KIT Delta 417-419 insY lines have a comparable clonogenicity of about 7%, whereas the cells of the ROSA KIT D816V line are less clonogenic (percentage of clonogenic cells around 4%), which is in agreement with the slightly longer doubling time and the more mature appearance of the cells of the ROSA KIT D816V line.

Moreover, the inventors analysed the structure of the KIT receptor in the 3 ROSA KIT WT, ROSA KIT Delta 417-419 insY and ROSA KIT D816V lines. To do so, the total RNA was extracted from the cells of each line using an RNeasy Mini kit (Qiagen SA, Courtaboeuf, France). The RNA was reverse transcribed to cDNA using a StrataScript first strand synthesis system (Stratagene, Massy, France) and random hexamer primers in a total volume of 25 ml, according to the manufacturer's instructions. The KIT coding sequences were then amplified by PCR from 2.5 ml of cDNA, using HotStarTaq DNA polymerase (Qiagen SA) and the primers already published (Bodemer C et al., J Invest Dermatol. 2010 March, 130(3): 804-815), by applying 40 cycles at 94° C. for 30 seconds, 57° C. for 30 seconds, and 72° C. for 45 seconds. The PCR products were purified using a GeneClean III kit (Qbiogene, Illkirch-Graffenstaden, France), and all the KIT coding regions were directly sequenced using a BigDye Terminator v1.1 kit (Applied Biosystems, Courtaboeuf, France), the published sequencing primers (see above, PCR primers) and an ABI Prism 3100 sequencer (Applied Biosystems).

The results obtained confirm the presence of wild-type KIT in the 3 ROSA KIT WT, ROSA KIT Delta 417-419 insY and ROSA KIT D816V lines. In addition, for the ROSA D816V line, the KIT sequencing shows that codon 816 of WT KIT (GAC) has been replaced with GTC. For the ROSA KIT Delta 417-419 insY line, the KIT sequencing shows that codons 417/418/419 of WT KIT (ACTTACGAC) have been replaced with the TAC codon. These results show that the ROSA KIT WT line indeed exhibits only a wild-type KIT, explaining its dependence with respect to SCF for its growth, whereas the expected KIT structure is found in the ROSA KIT Delta 417-419 insY and ROSA KIT D816V lines, which could explain their independence with respect to SCF for their proliferation.

The presence of KIT and its phosphorylation state were then verified, using the Western blotting method, in the three ROSA KIT WT, ROSA KIT Delta 417-419 insY and ROSA KIT D816V lines, treated or not treated with recombinant human SCF (80 ng/ml), in comparison with the HMC-1.2 line. The results of these experiments, presented in FIG. 14, show that the KIT protein is spontaneously present in the 4 lines. Furthermore, there is a constitutive phosphorylation of KIT in the HMC-1.2 line, and also in the ROSA KIT Delta 417-419 insY and ROSA KIT D816V lines, this being the case in the absence of SCF. On the other hand, KIT is phosphorylated on tyrosine only in the presence of SCF. These results confirm that the independence with respect to SCF of the ROSA KIT Delta 417-419 insY and ROSA KIT D816V lines is indeed due to a constitutive phosphorylation of the mutated KIT receptor in these two lines.

Finally, the inventors evaluated the effect of two molecules which inhibit tyrosine kinase activity, imatinib and dasatinib (both supplied by *Sequoia* Research), on the proliferation of the 3 ROSA KIT WT, ROSA KIT D816V and ROSA KIT Delta 417-419 insY lines. To do this, the cells were seeded at a starting concentration of $3 \times 10^5$ cells per ml in 96-well plates (100 µl per well) and incubated at 37° C. in an incubator (5% $CO_2$ in air) for 48 hours in the presence of 1 µM/l of imatinib or of dasatinib (in DMSO brought to a final concentration of 0.1%) or in the presence of DMSO alone (0.1% final concentration) in their usual culture medium (containing human SCF at 80 ng/ml for the ROSA KIT WT line but without SCF for the ROSA KIT D816V and ROSA KIT Delta 417-419 insY lines). At the end of this incubation, 10 µl of WST-1 (Roche Applied Science) are added to each well and the cells are incubated for a further 3 hours in an incubator at 37° C. The number of live cells is then measured for each condition by reading the absorbance at 450 nm using a Multiskan MS plate reader (Thermo LabSystems).

The results obtained for each line (presented in FIG. 15) are expressed as % of live cells (the condition DMSO alone at 0.1% final concentration being considered to contain 100% of live cells).

The results obtained are completely in accordance with those of the literature (Shah et al. Blood. 2006 Jul. 1, 108(1): 286-91). Specifically, they show that both the cells of the ROSA KIT WT line and those of the ROSA KIT Delta 417-419 insY line are sensitive to the inhibitory effect of Imatinib (inhibitor of WT KIT or of mutated KIT at the level of the extracellular domain of KIT) and to the inhibitory effect of dasatinib. On the other hand, and as expected, imatinib is incapable of inhibiting the proliferation of the cells of the ROSA KIT D816V line.

These results thus show that these three cell lines are perfectly suited to differential screening for inhibitors of the various forms of wild-type KIT or of mutated KIT.

REFERENCES

1. Razin E, Ihle J N, Seldin D, Mencia-Huerta J M, Katz H R, LeBlanc P A, Hein A, Caulfield J P, Austen K F, Stevens R L. Interleukin 3: A differentiation and growth factor for the mouse mast cell that contains chondroitin sulfate E proteoglycan. J Immunol. 1984 March; 132(3): 1479-86.
2. Levi-Schaffer F, Austen K F, Gravallese P M, Stevens R L. Coculture of interleukin 3-dependent mouse mast cells with fibroblasts results in a phenotypic change of the mast cells. Proc Natl Acad Sci USA. 1986 September; 83(17): 6485-8.
3. Tadokoro K, Stadler B M, De Weck A L. Factor-dependent in vitro growth of human normal bone marrow-derived basophil-like cells. J Exp Med. 1983 Sep. 1; 158(3): 857-71.
4. Moqbel R, Wakelin D, MacDonald A J, King S J, Grencis R K, Kay A B. Release of leukotrienes during rapid expulsion of *Trichinella spiralis* from immune rats. Immunology. 1987 March; 60(3): 425-30.
5. Dayton E T, Pharr P, Ogawa M, Serafin W E, Austen K F, Levi-Schaffer F, Stevens R L. 3T3 fibroblasts induce cloned interleukin 3-dependent mouse mast cells to resemble connective tissue mast cells in granular constituency. Proc Natl Acad Sci USA. 1988 January; 85(2): 569-72.
6. Butterfield J H, Weiler D, Dewald G, Gleich G J. Establishment of an immature mast cell line from a patient with mast cell leukaemia. Leuk Res. 1988; 12(4): 345-55.
7. Befus A D. Mast cells are that polymorphic! Reg Immunol. 1989 May-June; 2(3): 176-87.
8. Burd P R, Rogers H W, Gordon J R, Martin C A, Jayaraman S, Wilson S D, Dvorak A M, Galli S J, Dorf M E. Interleukin 3-dependent and -independent mast cells stimulated with IgE and antigen express multiple cytokines. J Exp Med. 1989 Jul. 1; 170(1): 245-57.
9. Furitsu T, Saito H, Dvorak A M, Schwartz L B, Irani A M, Burdick J F, Ishizaka K, Ishizaka T. Development of human mast cells in vitro. Proc Natl Acad Sci USA. 1989 December; 86(24): 10039-43.
10. Galli S J. New insights into "the riddle of the mast cells": microenvironmental regulation of mast cell development and phenotypic heterogeneity. Lab Invest. 1990 January; 62(1): 5-33.
11. Schaeffer W I. Terminology associated with cell, tissue, and organ culture, molecular biology, and molecular genetics. Tissue Culture Association Terminology Committee. In Vitro Cell Dev Biol. 1990 January; 26(1): 97-101.
12. Furitsu T, Tsujimura T, Tono T, Ikeda H, Kitayama H, Koshimizu U, Sugahara H, Butterfield J H, Ashman L K, Kanayama Y. Identification of mutations in the coding sequence of the proto-oncogene c-kit in a human mast cell leukaemia cell line causing ligand-independent activation of c-kit product. J Clin Invest. 1993 October; 92(4): 1736-44.
13. Valent P. The riddle of the mast cell: kit(CD117)-ligand as the missing link? Immunol Today. 1994 March; 15(3): 111-4.
14. Abraham S N, Malaviya R. Mast cells in infection and immunity. Infect Immun. 1997 September; 65(9): 3501-8.
15. Kirshenbaum A S, Goff J P, Semere T, Foster B, Scott L M, Metcalfe D D. Demonstration that human mast cells arise from a progenitor cell population that is CD34(+), c-kit(+), and expresses aminopeptidase N (CD13). Blood. 1999 Oct. 1; 94(7): 2333-42.
16. Varadaradjalou S, Féger F, Thieblemont N, Hamouda N B, Pleau J M, Dy M, Arock M. Toll-like receptor 2 (TLR2) and TLR4 differentially activate human mast cells. Eur J Immunol. 2003 April; 33(4): 899-906.
17. Kirshenbaum A S, Akin C, Wu Y, Rottem M, Goff J P, Beaven M A, Rao V K, Metcalfe D D. Characterization of novel stem cell factor responsive human mast cell lines LAD 1 and 2 established from a patient with mast cell sarcoma/leukaemia; activation following aggregation of FcepsilonR1 or FcgammaRI. Leuk Res. 2003; 27(8): 677-82.
18. Yoshikubo T, Inoue T, Noguchi M, Okabe H. Differentiation and maintenance of mast cells from CD34(+) human cord blood cells. Exp Hematol. 2006; 34(3): 320-9.
19. Valent P, Akin C, Escribano L, Födinger M, Hartmann K, Brockow K, Castells M, Sperr W R, Kluin-Nelemans H C, Hamdy N A, Lortholary O, Robyn J, van Doormaal J, Sotlar K, Hauswirth A W, Arock M, Hermine O, Hellmann A, Triggiani M, Niedoszytko M, Schwartz L B, Orfao A, Horny H P, Metcalfe D D. Standards and standardization in mastocytosis: consensus statements on diagnostics, treatment recommendations and response criteria. Eur J Clin Invest. 2007; 37(6): 435-53.
20. Malbec O, Roget K, Schiffer C, Iannascoli B, Dumas A R, Arock M, Daëron M. Peritoneal cell-derived mast cells: an in vitro model of mature serosal-type mouse mast cells. J Immunol. 2007; 178(10): 6465-75.
21. Mayerhofer M, Gleixner K V, Hoelbl A, Florian S, Hoermann G, Aichberger K J, Bilban M, Esterbauer H, Krauth M T, Sperr W R, Longley J B, Kralovics R, Moriggl R, Zappulla J, Liblau R S, Schwarzinger I, Sexl V, Sillaber C, Valent P. Unique effects of KIT D816V in BaF3 cells: induction of cluster formation, histamine synthesis, and early mast cell differentiation antigens. J Immunol. 2008 Apr. 15; 180(8): 5466-76.
22. Bodemer C, Hermine O, Palmérini F, Yang Y, Grandpeix-Guyodo C, Leventhal P S, Hadj-Rabia S, Nasca L, Georgin-Lavialle S, Cohen-Akenine A, Launay J M, Barete S, Feger F, Arock M, Catteau B, Sans B, Stalder J F, Skowron F, Thomas L, Lorette G, Plantin P, Bordigoni P, Lortholary O, de Prost Y, Moussy A, Sobol H, Dubreuil P. Pediatric mastocytosis is a clonal disease associated with D816V and other activating c-KIT mutations. J Invest Dermatol. 2010; 30(3): 804-15.
23. Laidlaw T M, Steinke J W, Tiñana A M, Feng C, Xing W, Lam B K, Paruchuri S, Boyce J A, Borish L. Characterization of a novel human mast cell line that responds to stem cell factor and expresses functional FceRI. J Allergy Clin Immunol. 2011; 127(3): 815-22.

The invention claimed is:

1. A human mast cell line having the following morphological, ultrastructural and phenotypic characteristics: a) presence of metachromatic intra-cytoplasmic granulations, and b) expression of FcεR1 and wild-type KIT (CD117) receptors, and of CD33, CD203c and CD300a markers, and also the following functional characteristics, strict dependence with respect to SCF for its survival and its growth; a doubling time of at most 72 hours; and proliferation for a period of at least six months, wherein said human mast cell line is identified as ROSA KIT WT as registered under deposit number CNCM I-4551 with the Collection Nationale de Cultures de Micro-organismes (CNCM) on 2 Nov. 2011.

2. A cell line derived from the human mast cell line identified as ROSA KIT WT according to claim 1, said derived cell line being identified as ROSA KIT D816V as registered under deposit number CNCM I-4552 with the CNCM on 2 Nov. 2011.

3. A cell line derived from the human mast cell line identified as ROSA KIT WT according to claim 1, said derived cell line being identified as ROSA KIT Delta 417-419 insY as registered under deposit number CNCM I-4553 with the CNCM on 2 Nov. 2011.

4. A kit for screening for an agent of interest, comprising i) the mast cell line according to claim 1 and; ii) a supplementary product chosen from one or more culture media, one or more maintenance media, one or more growth factors enabling or promoting the culturing of the mast cells; and any combination of said products.

5. A kit for screening for an agent of interest, comprising i) the mast cell line according to claim 2 and; ii) a supplementary product chosen from one or more culture media, one or more maintenance media, one or more growth factors enabling or promoting the culturing of the mast cells; and any combination of said products.

* * * * *

SEQUENCE LISTING

```
<160> NUMBER OF SEQ ID NOS: 6

<210> SEQ ID NO 1
<211> LENGTH: 2931
<212> TYPE: DNA
<213> ORGANISM: Homo sapiens
<220> FEATURE:
<221> NAME/KEY: exon
<222> LOCATION: (1237)..(1352)
<223> OTHER INFORMATION: Exon 8
<220> FEATURE:
<221> NAME/KEY: exon
<222> LOCATION: (1353)..(1547)
<223> OTHER INFORMATION: Exon 9

<400> SEQUENCE: 1
atgagaggcg ctcgcggcgc ctgggatttt ctctgcgttc tgctcctact gcttcgcgtc     60
cagacaggct cttctcaacc atctgtgagt ccaggggaac cgtctccacc atccatccat    120
ccaggaaaat cagacttaat agtccgcgtg ggcgacgaga ttaggctgtt atgcactgat    180
ccgggctttg tcaaatggac ttttgagatc ctggatgaaa cgaatgagaa taagcagaat    240
gaatggatca cggaaaaggc agaagccacc aacaccggca aatacacgtg caccaacaaa    300
cacggcttaa gcaattccat ttatgtgttt gttagagatc ctgccaagct tttccttgtt    360
gaccgctcct tgtatgggaa agaagacaac gacacgctgg tccgctgtcc tctcacagac    420
ccagaagtga ccaattattc cctcaagggg tgccagggga gcctcttcc caaggacttg    480 aggtttattc tgaccccaa ggcgggcatc atgatcaaaa gtgtgaaacg cgcctaccat    540
cggctctgtc tgcattgttc tgtggaccag gagggcaagt cagtgctgtc ggaaaaattc    600
atcctgaaag tgaggccagc cttcaaagct gtgcctgttg tgtctgtgtc caaagcaagc    660
tatcttctta gggaagggga agaattcaca gtgacgtgca atataaaaga tgtgtctagt    720
tctgtgtact caacgtggaa aagagaaaac agtcagacta aactacagga gaatataat    780 agctggcatc acggtgactt caattatgaa cgtcaggcaa cgttgactat cagttcagcg    840
agagttaatg attctggagt gttcatgtgt tatgccaata tacttttgg atcagcaaat    900 gtcacaacaa ccttggaagt agtagataaa ggattcatta atatcttccc catgataaac    960
actacagtat ttgtaaacga tggagaaaat gtagatttga ttgttgaata tgaagcattc   1020
cccaaacctg aacaccagca gtggatctat atgaacagaa ccttcactga taatgggaa   1080 gattatccca gtctgagaa tgaaagtaat atcagatacg taagtgaact tcatctaacg   1140
agattaaaag gcaccgaagg aggcacttac acattcctag tgtccaattc tgacgtcaat   1200
gctgccatag catttaatgt ttatgtgaat acaaaa cca gaa atc ctg act tac    1254
```

```
                    Pro Glu Ile Leu Thr Tyr
                     1               5
gac agg ctc gtg aat ggc atg ctc caa tgt gtg gca gca gga ttc cca    1302
Asp Arg Leu Val Asn Gly Met Leu Gln Cys Val Ala Ala Gly Phe Pro
         10                  15                  20 gag ccc aca ata gat tgg tat ttt tgt cca gga act gag cag aga tgc    1350
Glu Pro Thr Ile Asp Trp Tyr Phe Cys Pro Gly Thr Glu Gln Arg Cys
             25                  30                  35 tc  t gct tct gta ctg cca gtg gat gtg cag aca cta aac tca tct ggg  1398
Ser   Ala Ser Val Leu Pro Val Asp Val Gln Thr Leu Asn Ser Ser Gly
         40                  45                  50 cca ccg ttt gga aag cta gtg gtt cag agt tct ata gat tct agt gca    1446
Pro Pro Phe Gly Lys Leu Val Val Gln Ser Ser Ile Asp Ser Ser Ala
 55                  60                  65                  70 ttc aag cac aat ggc acg gtt gaa tgt aag gct tac aac gat gtg ggc    1494
Phe Lys His Asn Gly Thr Val Glu Cys Lys Ala Tyr Asn Asp Val Gly
                 75                  80                  85 aag act tct gcc tat ttt aac ttt gca ttt aaa ggt aac aac aaa gag    1542
Lys Thr Ser Ala Tyr Phe Asn Phe Ala Phe Lys Gly Asn Asn Lys Glu
         90                  95                 100 caa at ccatccccac accctgttca ctcctttgct gattggtttc gtaatcgtag      1597
Gln ctggcatgat gtgcattatt gtgatgattc tgacctacaa atatttacag aaacccatgt  1657
atgaagtaca gtggaaggtt gttgaggaga taaatggaaa caattatgtt tacatagacc  1717
caacacaact tccttatgat cacaaatggg agtttcccag aaacaggctg agttttggga  1777
aaaccctggg tgctggagct ttcgggaagg ttgttgaggc aactgctat ggcttaatta   1837
agtcagatgc ggccatgact gtcgctgtaa agatgctcaa gccgagtgcc catttgacag  1897
aacgggaagc cctcatgtct gaactcaaag tcctgagtta ccttggtaat cacatgaata  1957
ttgtgaatct acttggagcc tgcaccattg gagggcccac cctggtcatt acagaatatt  2017
gttgctatgg tgatcttttg aattttttga gaagaaaacg tgattcattt atttgttcaa  2077
agcaggaaga tcatgcagaa gctgcacttt ataagaatct tctgcattca aaggagtctt  2137
cctgcagcga tagtactaat gagtacatgg acatgaaacc tggagttcct atgttgtcc   2197
caaccaaggc cgacaaaagg agatctgtga aataggctc atacatagaa agagatgtga   2257
ctcccgccat catggaggat gacgagttgg ccctagactt agaagacttg ctgagctttt   2317
cttaccaggt ggcaaagggc atggctttcc tcgcctccaa gaattgtatt cacagagact  2377
tggcagccag aaatatcctc cttactcatg gtcggatcac aaagatttgt gattttggtc  2437
tagccagaga catcaagaat gattctaatt atgtggttaa aggaaacgct cgactacctg  2497
tgaagtggat ggcaccctgaa agcatttttca actgtgtata cacgtttgaa agtgacgtct  2557
ggtcctatgg gattttttctt tgggagctgt tctctttagg aagcagcccc tatcctggaa  2617
tgccggtcga ttctaagttc tacaagatga tcaaggaagg cttccggatg ctcagccctg  2677
aacacgcacc tgctgaaatg tatgacataa tgaagacttg ctgggatgca gatcccctaa   2737
aaagaccaac attcaagcaa attgttcagc taattgagaa gcagatttca gagagcacca  2797
atcatattta ctccaactta gcaaactgca gccccaaccg acagaagccc gtggtagacc  2857
attctgtgcg gatcaattct gtcggcagca ccgcttcctc ctcccagcct ctgcttgtgc  2917
acgacgatgt ctga                                                    2931

<210> SEQ ID NO 2
<211> LENGTH: 976
```

```
<212> TYPE: PRT
<213> ORGANISM: Homo sapiens
<220> FEATURE:
<221> NAME/KEY: DOMAIN
<222> LOCATION: (26)..(519)
<223> OTHER INFORMATION: extracellular domain
<220> FEATURE:
<221> NAME/KEY: DOMAIN
<222> LOCATION: (543)..(582)
<223> OTHER INFORMATION: juxtamembrane domain
<220> FEATURE:
<221> NAME/KEY: DOMAIN
<222> LOCATION: (762)..(937)
<223> OTHER INFORMATION: phosphotransferase domain

<400> SEQUENCE: 2
```

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

-continued

```
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
    450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
            500                 505                 510
Lys Glu Gln Ile His Pro His Thr Leu Phe Thr Pro Leu Leu Ile Gly
        515                 520                 525
Phe Val Ile Val Ala Gly Met Met Cys Ile Ile Val Met Ile Leu Thr
    530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
            580                 585                 590
Lys Thr Leu Gly Ala Gly Ala Phe Gly Lys Val Val Glu Ala Thr Ala
        595                 600                 605
Tyr Gly Leu Ile Lys Ser Asp Ala Ala Met Thr Val Ala Val Lys Met
    610                 615                 620
Leu Lys Pro Ser Ala His Leu Thr Glu Arg Glu Ala Leu Met Ser Glu
625                 630                 635                 640
Leu Lys Val Leu Ser Tyr Leu Gly Asn His Met Asn Ile Val Asn Leu
                645                 650                 655
Leu Gly Ala Cys Thr Ile Gly Gly Pro Thr Leu Val Ile Thr Glu Tyr
            660                 665                 670
Cys Cys Tyr Gly Asp Leu Leu Asn Phe Leu Arg Arg Lys Arg Asp Ser
        675                 680                 685
Phe Ile Cys Ser Lys Gln Glu Asp His Ala Glu Ala Ala Leu Tyr Lys
    690                 695                 700
Asn Leu Leu His Ser Lys Glu Ser Ser Cys Ser Asp Ser Thr Asn Glu
705                 710                 715                 720
Tyr Met Asp Met Lys Pro Gly Val Ser Tyr Val Val Pro Thr Lys Ala
                725                 730                 735
Asp Lys Arg Arg Ser Val Arg Ile Gly Ser Tyr Ile Glu Arg Asp Val
            740                 745                 750
```

-continued

```
Thr Pro Ala Ile Met Glu Asp Asp Glu Leu Ala Ile Asp Leu Glu Asp
            755                 760                 765
Leu Leu Ser Phe Ser Tyr Gln Val Ala Lys Gly Met Ala Phe Leu Ala
        770                 775                 780
Ser Lys Asn Cys Ile His Arg Asp Leu Ala Ala Arg Asn Ile Leu Leu
785                 790                 795                 800
Thr His Gly Arg Ile Thr Lys Ile Cys Asp Phe Gly Leu Ala Arg Asp
                805                 810                 815
Ile Lys Asn Asp Ser Asn Tyr Val Val Lys Gly Asn Ala Arg Leu Pro
            820                 825                 830
Val Lys Trp Met Ala His Glu Ser Ile Phe Asn Cys Val Tyr Thr Phe
        835                 840                 845
Glu Ser Asp Val Trp Ser Tyr Gly Ile Phe Leu Trp Glu Leu Phe Ser
850                 855                 860
Leu Gly Ser Ser Pro Tyr Pro Gly Met Pro Val Asp Ser Lys Phe Tyr
865                 870                 875                 880
Lys Met Ile Lys Glu Gly Phe Arg Met Leu Ser Pro Glu His Ala Pro
                885                 890                 895
Ala Glu Met Tyr Asp Ile Met Lys Thr Cys Trp Asp Ala Asp Pro Leu
            900                 905                 910
Lys Arg Pro Thr Phe Lys Gln Ile Val Gln Leu Ile Glu Lys Gln Ile
        915                 920                 925
Ser Glu Ser Thr Asn His Ile Tyr Ser Asn Leu Ala Asn Cys Ser Pro
930                 935                 940
Asn Arg Gln Lys Pro Val Val Asp His Ser Val Arg Ile Asn Ser Val
945                 950                 955                 960
Gly Ser Thr Ala Ser Ser Ser Gln Pro Leu Leu Val His Asp Asp Val
                965                 970                 975

<210> SEQ ID NO 3
<211> LENGTH: 2919
<212> TYPE: DNA
<213> ORGANISM: Homo sapiens
<220> FEATURE:
<221> NAME/KEY: misc_feature
<223> OTHER INFORMATION: KIT D816V
<220> FEATURE:
<221> NAME/KEY: misc_feature
<222> LOCATION: (2434)..(2436)
<223> OTHER INFORMATION: mutation
<400> SEQUENCE: 3
atgagaggcg ctcgcggcgc ctgggatttt ctctgcgttc tgctcctact gcttcgcgtc      60
cagacaggct cttctcaacc atctgtgagt ccaggggaac cgtctccacc atccatccat     120
ccaggaaaat cagacttaat agtccgcgtg ggcgacgaga ttaggctgtt atgcactgat     180
ccgggctttg tcaaatggac ttttgagatc ctggatgaaa cgaatgagaa taagcagaat     240
gaatggatca cggaaaaggc agaagccacc aacaccggca atacacgtgt gaccaacaaa     300
cacggcttaa gcaattccat ttatgtgttt gttagagatc ctgccaagct tttccttgtt     360
gaccgctcct tgtatgggaa agaagacaac gacacgctgg tccgctgtcc tctcacagac     420
ccagaagtga ccaattattc cctcaagggg tgccagggga gcctcttcc caaggacttg     480 aggtttattc tgaccccaa ggcgggcatc atgatcaaaa gtgtgaaacg cgcctaccat     540
cggctctgtc tgcattgttc tgtggaccag gagggcaagt cagtgctgtc ggaaaaattc     600
atcctgaaag tgaggccagc cttcaaagct gtgcctgttg tgtctgtgtc caaagcaagc     660
```

| | |
|---|---|
| tatcttctta gggaagggga agaattcaca gtgacgtgca caataaaaga tgtgtctagt | 720 |
| tctgtgtact caacgtggaa aagagaaaac agtcagacta aactacagga gaaatataat | 780 |
| agctggcatc acggtgactt caattatgaa cgtcaggcaa cgttgactat cagttcagcg | 840 |
| agagttaatg attctggagt gttcatgtgt tatgccaata atactttttgg atcagcaaat | 900 |
| gtcacaacaa ccttggaagt agtagataaa ggattcatta atatcttccc catgataaac | 960 |
| actacagtat ttgtaaacga tggagaaaat gtagatttga ttgttgaata tgaagcattc | 1020 |
| cccaaacctg aacaccagca gtggatctat atgaacagaa ccttcactga taaatgggaa | 1080 |
| gattatccca gtctgagaa tgaaagtaat atcagatacg taagtgaact tcatctaacg | 1140 |
| agattaaaag gcaccgaagg aggcacttac acattcctag tgtccaattc tgacgtcaat | 1200 |
| gctgccatag catttaatgt ttatgtgaat acaaaaccag aaatcctgac ttacgacagg | 1260 |
| ctcgtgaatg gcatgctcca atgtgtggca gcaggattcc cagagcccac aatagattgg | 1320 |
| tattttttgtc caggaactga gcagagatgc tctgcttctg tactgccagt ggatgtgcag | 1380 |
| acactaaact catctgggcc accgtttgga aagctagtgg ttcagagttc tatagattct | 1440 |
| agtgcattca agcacaatgg cacggttgaa tgtaaggctt acaacgatgt gggcaagact | 1500 |
| tctgcctatt ttaactttgc atttaaagag caaatccatc cccacaccct gttcactcct | 1560 |
| ttgctgattg gtttcgtaat cgtagctggc atgatgtgca ttattgtgat gattctgacc | 1620 |
| tacaaatatt tacagaaacc catgtatgaa gtacagtgga aggttgttga ggagataaat | 1680 |
| ggaaacaatt atgtttacat agacccaaca caacttcctt atgatcacaa atgggagttt | 1740 |
| cccagaaaca ggctgagttt tgggaaaacc ctgggtgctg gagctttcgg gaaggttgtt | 1800 |
| gaggcaactg cttatggctt aattaagtca gatgcggcca tgactgtcgc tgtaaagatg | 1860 |
| ctcaagccga gtgcccattt gacagaacgg gaagccctca tgtctgaact caaagtcctg | 1920 |
| agttaccttg gtaatcacat gaatattgtg aatctacttg gagcctgcac cattggaggg | 1980 |
| cccacccctgg tcattacaga atattgttgc tatggtgatc tttttgaattt tttgagaaga | 2040 |
| aaacgtgatt catttatttg ttcaaagcag gaagatcatg cagaagctgc actttataag | 2100 |
| aatcttctgc attcaaagga gtcttcctgc agcgatagta ctaatgagta catggacatg | 2160 |
| aaacctggag tttcttatgt tgtcccaacc aaggccgaca aaaggagatc tgtgagaata | 2220 |
| ggctcataca tagaaagaga tgtgactccc gccatcatgg aggatgacga gttggccta | 2280 |
| gacttagaag acttgctgag ctttttcttac caggtggcaa agggcatggc tttcctcgcc | 2340 |
| tccaagaatt gtattcacag agacttggca gccagaaata tcctccttac tcatggtcgg | 2400 |
| atcacaaaga tttgtgattt tggtctagcc agagtcatca agaatgattc taattatgtg | 2460 |
| gttaaaggaa acgctcgact acctgtgaag tggatggcac ctgaaagcat tttcaactgt | 2520 |
| gtatacacgt ttgaaagtga cgtctggtcc tatgggattt ttctttggga gctgttctct | 2580 |
| ttaggaagca gccccctatcc tggaatgccg gtcgattcta gttctacaa gatgatcaag | 2640 |
| gaaggcttcc ggatgctcag ccctgaacac gcacctgctg aaatgtatga cataatgaag | 2700 |
| acttgctggg atgcagatcc cctaaaaaga ccaacattca agcaaattgt tcagctaatt | 2760 |
| gagaagcaga tttcagagag caccaatcat atttactcca acttagcaaa ctgcagcccc | 2820 |
| aaccgacaga agcccgtggt agaccattct gtgcggatca attctgtcgg cagcaccgct | 2880 |
| tcctcctccc agcctctgct tgtgcacgac gatgtctga | 2919 |

<210> SEQ ID NO 4
<211> LENGTH: 976

```
<212> TYPE: PRT
<213> ORGANISM: Homo sapiens
<220> FEATURE:
<221> NAME/KEY: MISC_FEATURE
<223> OTHER INFORMATION: KIT D816V protein
<220> FEATURE:
<221> NAME/KEY: MISC_FEATURE
<222> LOCATION: (816)..(816)
<223> OTHER INFORMATION: Mutation

<400> SEQUENCE: 4

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
```

```
              355                 360                 365
Ser Asn Ile Arg Tyr Val Ser Glu Leu His Leu Thr Arg Leu Lys Gly
            370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
            435                 440                 445
Arg Cys Ser Ala Ser Val Leu Pro Val Asp Val Gln Thr Leu Asn Ser
            450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
            500                 505                 510
Lys Glu Gln Ile His Pro His Thr Leu Phe Thr Pro Leu Leu Ile Gly
            515                 520                 525
Phe Val Ile Val Ala Gly Met Met Cys Ile Ile Val Met Ile Leu Thr
            530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
            580                 585                 590
Lys Thr Leu Gly Ala Gly Ala Phe Gly Lys Val Val Glu Ala Thr Ala
            595                 600                 605
Tyr Gly Leu Ile Lys Ser Asp Ala Ala Met Thr Val Ala Val Lys Met
            610                 615                 620
Leu Lys Pro Ser Ala His Leu Thr Glu Arg Glu Ala Leu Met Ser Glu
625                 630                 635                 640
Leu Lys Val Leu Ser Tyr Leu Gly Asn His Met Asn Ile Val Asn Leu
                645                 650                 655
Leu Gly Ala Cys Thr Ile Gly Gly Pro Thr Leu Val Ile Thr Glu Tyr
            660                 665                 670
Cys Cys Tyr Gly Asp Leu Leu Asn Phe Leu Arg Arg Lys Arg Asp Ser
            675                 680                 685
Phe Ile Cys Ser Lys Gln Glu Asp His Ala Glu Ala Leu Tyr Lys
            690                 695                 700
Asn Leu Leu His Ser Lys Glu Ser Ser Cys Ser Asp Ser Thr Asn Glu
705                 710                 715                 720
Tyr Met Asp Met Lys Pro Gly Val Ser Tyr Val Val Pro Thr Lys Ala
                725                 730                 735
Asp Lys Arg Arg Ser Val Arg Ile Gly Ser Tyr Ile Glu Arg Asp Val
            740                 745                 750
Thr Pro Ala Ile Met Glu Asp Asp Glu Leu Ala Ile Asp Leu Glu Asp
            755                 760                 765
Leu Leu Ser Phe Ser Tyr Gln Val Ala Lys Gly Met Ala Phe Leu Ala
            770                 775                 780
```

```
Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Val
            805                 810                 815

Ile Lys Asn Asp Ser Asn Tyr Val Val Lys Gly Asn Ala Arg Leu Pro
            820                 825                 830

Val Lys Trp Met Ala His Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
            885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 5
<211> LENGTH: 2913
<212> TYPE: DNA
<213> ORGANISM: Homo sapiens
<220> FEATURE:
<221> NAME/KEY: misc_feature
<223> OTHER INFORMATION: KIT Delta 417-419 InsY
<220> FEATURE:
<221> NAME/KEY: misc_feature
<222> LOCATION: (417)..(419)
<223> OTHER INFORMATION: Mutation

<400> SEQUENCE: 5
atgagaggcg ctcgcggcgc ctgggatttt ctctgcgttc tgctcctact gcttcgcgtc      60
cagacaggct cttctcaacc atctgtgagt ccaggggaac cgtctccacc atccatccat     120
ccaggaaaat cagacttaat agtccgcgtg ggcgacgaga ttaggctgtt atgcactgat     180
ccgggctttg tcaaatggac ttttgagatc ctggatgaaa cgaatgagaa taagcagaat     240
gaatggatca cggaaaaggc agaagccacc aacaccggca aatacacgtg caccaacaaa     300
cacggcttaa gcaattccat ttatgtgttt gttagagatc ctgccaagct tttccttgtt     360
gaccgctcct tgtatgggaa agaagacaac gacacgctgg tccgctgtcc tctcacagac     420
ccagaagtga ccaattattc cctcaagggg tgccagggga gcctcttcc caaggacttg     480 aggtttattc ctgaccccaa ggcgggcatc atgatcaaaa gtgtgaaacg cgcctaccat     540
cggctctgtc tgcattgttc tgtggaccag gagggcaagt cagtgctgtc ggaaaaattc     600
atcctgaaag tgaggccagc cttcaaagct gtgcctgttg tgtctgtgtc caaagcaagc     660
tatcttctta gggaagggga agaattcaca gtgacgtgca ataaaagga tgtgtctagt     720 tctgtgtact caacgtggaa aagagaaaac agtcagacta actacagga gaaatataat     780 agctggcatc acggtgactt caattatgaa cgtcaggcaa cgttgactat cagttcagcg     840
```

```
agagttaatg attctggagt gttcatgtgt tatgccaata atacttttgg atcagcaaat      900
gtcacaacaa ccttggaagt agtagataaa ggattcatta atatcttccc catgataaac      960
actacagtat ttgtaaacga tggagaaaat gtagatttga ttgttgaata tgaagcattc     1020
cccaaacctg aacaccagca gtggatctat atgaacagaa ccttcactga taaatgggaa     1080
gattatccca gtctgagaa tgaaagtaat atcagatacg taagtgaact tcatctaacg     1140
agattaaaag gcaccgaagg aggcacttac acattcctag tgtccaattc tgacgtcaat     1200
gctgccatag catttaatgt ttatgtgaat acaaaccag aaatcctgta caggctcgtg      1260
aatggcatgc tccaatgtgt ggcagcagga ttcccagagc ccacaataga ttggtatttt     1320
tgtccaggaa ctgagcagag atgctctgct tctgtactgc cagtggatgt gcagacacta     1380
aactcatctg ggccaccgtt tggaaagcta gtggttcaga ttctataga ttctagtgca      1440 ttcaagcaca atggcacggt tgaatgtaag gcttacaacg atgtgggcaa gacttctgcc     1500
tattttaact ttgcatttaa agagcaaatc catccccaca ccctgttcac tcctttgctg     1560
attggtttcg taatcgtagc tggcatgatg tgcattattg tgatgattct gacctacaaa     1620
tatttacaga aacccatgta tgaagtacag tggaaggttg ttgaggagat aaatggaaac     1680
aattatgttt acatagaccc aacacaactt cctttatgatc acaaatggga gtttcccaga     1740
aacaggctga gttttgggaa accctgggt gctggagctt cgggaaggt tgttgaggca      1800 actgcttatg gcttaattaa gtcagatgcg gccatgactg tcgctgtaaa gatgctcaag     1860
ccgagtgccc atttgacaga acgggaagcc ctcatgtctg aactcaaagt cctgagttac     1920
cttggtaatc acatgaatat tgtgaatcta cttggagcct gcaccattgg agggcccacc     1980
ctggtcatta cagaatattg ttgctatggt gatcttttga attttttgag aagaaaacgt     2040
gattcattta tttgttcaaa gcaggaagat catgcagaag ctgcactta taagaatctt      2100 ctgcattcaa aggagtcttc ctgcagcgat agtactaatg agtacatgga catgaaacct     2160
ggagtttctt atgttgtccc aaccaaggcc gacaaaagga gatctgtgag aataggctca     2220
tacatagaaa gagatgtgac tcccgccatc atggaggatg acgagttggc cctagactta     2280
gaagacttgc tgagcttttc ttaccaggtg gcaaagggca tggctttcct cgcctccaag     2340
aattgtattc acagagactt ggcagccaga aatatcctcc ttactcatgg tcggatcaca     2400
aagatttgtg attttggtct agccagagac atcaagaatt attctaatta tgtggttaaa     2460
ggaaacgctc gactacctgt gaagtggatg gcacctgaaa gcattttcaa ctgtgtatac     2520
acgtttgaaa gtgacgtctg gtcctatggg attttctttt gggagctgtt ctctttagga     2580
agcagcccct atcctggaat gccggtcgat tctaagttct acaagatgat caaggaaggc     2640
ttccggatgc tcagccctga acacgcacct gctgaaatgt atgacataat gaagacttgc     2700
tgggatgcag atccctaaa aagaccaaca ttcaagcaaa ttgttcagct aattgagaag      2760
cagatttcag agagcaccaa tcatatttac tccaacttag caactgcag ccccaaccga     2820 cagaagcccg tggtagacca ttctgtgcgg atcaattctg tcggcagcac cgcttcctcc     2880
tcccagcctc tgcttgtgca cgacgatgtc tga                                  2913
```

<210> SEQ ID NO 6
<211> LENGTH: 974
<212> TYPE: PRT
<213> ORGANISM: Homo sapiens
<220> FEATURE:
<221> NAME/KEY: MISC_FEATURE
<223> OTHER INFORMATION: KIT Delta 417-419 insY

```
<220> FEATURE:
<221> NAME/KEY: MISC_FEATURE
<222> LOCATION: (417)..(419)
<223> OTHER INFORMATION: Mutation

<400> SEQUENCE: 6
```

| | | | | | | | | | | | | | | | |
|---|---|---|---|---|---|---|---|---|---|---|---|---|---|---|---|
| Met | Arg | Gly | Ala | Arg | Gly | Ala | Trp | Asp | Phe | Leu | Cys | Val | Leu | Leu | Leu |
| 1 | | | | 5 | | | | | 10 | | | | | 15 | |
| Leu | Leu | Arg | Val | Gln | Thr | Gly | Ser | Ser | Gln | Pro | Ser | Val | Ser | Pro | Gly |
| | | | 20 | | | | | 25 | | | | | 30 | | |
| Glu | Pro | Ser | Pro | Ser | Ile | His | Pro | Gly | Lys | Ser | Asp | Leu | Ile | Val | |
| | | 35 | | | | 40 | | | | | 45 | | | | |
| Arg | Val | Gly | Asp | Glu | Ile | Arg | Leu | Leu | Cys | Thr | Asp | Pro | Gly | Phe | Val |
| | 50 | | | | | 55 | | | | | 60 | | | | |
| Lys | Trp | Thr | Phe | Glu | Ile | Leu | Asp | Glu | Thr | Asn | Glu | Asn | Lys | Gln | Asn |
| 65 | | | | | 70 | | | | | 75 | | | | | 80 |
| Glu | Trp | Ile | Thr | Glu | Lys | Ala | Glu | Ala | Thr | Asn | Thr | Gly | Lys | Tyr | Thr |
| | | | | 85 | | | | | 90 | | | | | 95 | |
| Cys | Thr | Asn | Lys | His | Gly | Leu | Ser | Asn | Ser | Ile | Tyr | Val | Phe | Val | Arg |
| | | | 100 | | | | | 105 | | | | | 110 | | |
| Asp | Pro | Ala | Lys | Leu | Phe | Leu | Val | Asp | Arg | Ser | Leu | Tyr | Gly | Lys | Glu |
| | | | 115 | | | | | 120 | | | | | 125 | | |
| Asp | Asn | Asp | Thr | Leu | Val | Arg | Cys | Pro | Leu | Thr | Asp | Pro | Glu | Val | Thr |
| | 130 | | | | | 135 | | | | | 140 | | | | |
| Asn | Tyr | Ser | Leu | Lys | Gly | Cys | Gln | Gly | Lys | Pro | Leu | Pro | Lys | Asp | Leu |
| 145 | | | | | 150 | | | | | 155 | | | | | 160 |
| Arg | Phe | Ile | Pro | Asp | Pro | Lys | Ala | Gly | Ile | Met | Ile | Lys | Ser | Val | Lys |
| | | | | 165 | | | | | 170 | | | | | 175 | |
| Arg | Ala | Tyr | His | Arg | Leu | Cys | Leu | His | Cys | Ser | Val | Asp | Gln | Glu | Gly |
| | | | 180 | | | | | 185 | | | | | 190 | | |
| Lys | Ser | Val | Leu | Ser | Glu | Lys | Phe | Ile | Leu | Lys | Val | Arg | Pro | Ala | Phe |
| | | | 195 | | | | | 200 | | | | | 205 | | |
| Lys | Ala | Val | Pro | Val | Val | Ser | Val | Ser | Lys | Ala | Ser | Tyr | Leu | Leu | Arg |
| | 210 | | | | | 215 | | | | | 220 | | | | |
| Glu | Gly | Glu | Glu | Phe | Thr | Val | Thr | Cys | Thr | Ile | Lys | Asp | Val | Ser | Ser |
| 225 | | | | | 230 | | | | | 235 | | | | | 240 |
| Ser | Val | Tyr | Ser | Thr | Trp | Lys | Arg | Glu | Asn | Ser | Gln | Thr | Lys | Leu | Gln |
| | | | | 245 | | | | | 250 | | | | | 255 | |
| Glu | Lys | Tyr | Asn | Ser | Trp | His | His | Gly | Asp | Phe | Asn | Tyr | Glu | Arg | Gln |
| | | | 260 | | | | | 265 | | | | | 270 | | |
| Ala | Thr | Leu | Thr | Ile | Ser | Ser | Ala | Arg | Val | Asn | Asp | Ser | Gly | Val | Phe |
| | | | 275 | | | | | 280 | | | | | 285 | | |
| Met | Cys | Tyr | Ala | Asn | Asn | Thr | Phe | Gly | Ser | Ala | Asn | Val | Thr | Thr | Thr |
| | 290 | | | | | 295 | | | | | 300 | | | | |
| Leu | Glu | Val | Val | Asp | Lys | Gly | Phe | Ile | Asn | Ile | Phe | Pro | Met | Ile | Asn |
| 305 | | | | | 310 | | | | | 315 | | | | | 320 |
| Thr | Thr | Val | Phe | Val | Asn | Asp | Gly | Glu | Asn | Val | Asp | Leu | Ile | Val | Glu |
| | | | | 325 | | | | | 330 | | | | | 335 | |
| Tyr | Glu | Ala | Phe | Pro | Lys | Pro | Glu | His | Gln | Gln | Trp | Ile | Tyr | Met | Asn |
| | | | 340 | | | | | 345 | | | | | 350 | | |
| Arg | Thr | Phe | Thr | Asp | Lys | Trp | Glu | Asp | Tyr | Pro | Lys | Ser | Glu | Asn | Glu |
| | | | 355 | | | | | 360 | | | | | 365 | | |
| Ser | Asn | Ile | Arg | Tyr | Val | Ser | Glu | Leu | His | Leu | Thr | Arg | Leu | Lys | Gly |
| | 370 | | | | | 375 | | | | | 380 | | | | |

-continued

```
Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
            405                 410                 415

Tyr Arg Leu Val Asn Gly Met Leu Gln Cys Val Ala Ala Gly Phe Pro
        420                 425                 430

Glu Pro Thr Ile Asp Trp Tyr Phe Cys Pro Gly Thr Glu Gln Arg Cys
    435                 440                 445

Ser Ala Ser Val Leu Pro Val Asp Val Gln Thr Leu Asn Ser Ser Gly
450                 455                 460

Pro Pro Phe Gly Lys Leu Val Val Gln Ser Ser Ile Asp Ser Ser Ala
465                 470                 475                 480

Phe Lys His Asn Gly Thr Val Glu Cys Lys Ala Tyr Asn Asp Val Gly
            485                 490                 495

Lys Thr Ser Ala Tyr Phe Asn Phe Ala Phe Lys Gly Asn Asn Lys Glu
        500                 505                 510

Gln Ile His Pro His Thr Leu Phe Thr Pro Leu Leu Ile Gly Phe Val
    515                 520                 525

Ile Val Ala Gly Met Met Cys Ile Ile Val Met Ile Leu Thr Tyr Lys
530                 535                 540

Tyr Leu Gln Lys Pro Met Tyr Glu Val Gln Trp Lys Val Val Glu Glu
545                 550                 555                 560

Ile Asn Gly Asn Asn Tyr Val Tyr Ile Asp Pro Thr Gln Leu Pro Tyr
            565                 570                 575

Asp His Lys Trp Glu Phe Pro Arg Asn Arg Leu Ser Phe Gly Lys Thr
        580                 585                 590

Leu Gly Ala Gly Ala Phe Gly Lys Val Val Glu Ala Thr Ala Tyr Gly
    595                 600                 605

Leu Ile Lys Ser Asp Ala Ala Met Thr Val Ala Val Lys Met Leu Lys
610                 615                 620

Pro Ser Ala His Leu Thr Glu Arg Glu Ala Leu Met Ser Glu Leu Lys
625                 630                 635                 640

Val Leu Ser Tyr Leu Gly Asn His Met Asn Ile Val Asn Leu Leu Gly
            645                 650                 655

Ala Cys Thr Ile Gly Gly Pro Thr Leu Val Ile Thr Glu Tyr Cys Cys
        660                 665                 670

Tyr Gly Asp Leu Leu Asn Phe Leu Arg Arg Lys Arg Asp Ser Phe Ile
    675                 680                 685

Cys Ser Lys Gln Glu Asp His Ala Glu Ala Leu Tyr Lys Asn Leu
690                 695                 700

Leu His Ser Lys Glu Ser Ser Cys Ser Asp Ser Thr Asn Glu Tyr Met
705                 710                 715                 720

Asp Met Lys Pro Gly Val Ser Tyr Val Val Pro Thr Lys Ala Asp Lys
            725                 730                 735

Arg Arg Ser Val Arg Ile Gly Ser Tyr Ile Glu Arg Asp Val Thr Pro
        740                 745                 750

Ala Ile Met Glu Asp Asp Glu Leu Ala Ile Asp Leu Glu Asp Leu Leu
    755                 760                 765

Ser Phe Ser Tyr Gln Val Ala Lys Gly Met Ala Phe Leu Ala Ser Lys
770                 775                 780

Asn Cys Ile His Arg Asp Leu Ala Ala Arg Asn Ile Leu Leu Thr His
785                 790                 795                 800

Gly Arg Ile Thr Lys Ile Cys Asp Phe Gly Leu Ala Arg Asp Ile Lys
```

```
            805                 810                 815
Asn Asp Ser Asn Tyr Val Val Lys Gly Asn Ala Arg Leu Pro Val Lys
            820                 825                 830

Trp Met Ala His Glu Ser Ile Phe Asn Cys Val Tyr Thr Phe Glu Ser
            835                 840                 845

Asp Val Trp Ser Tyr Gly Ile Phe Leu Trp Glu Leu Phe Ser Leu Gly
        850                 855                 860

Ser Ser Pro Tyr Pro Gly Met Pro Val Asp Ser Lys Phe Tyr Lys Met
865                 870                 875                 880

Ile Lys Glu Gly Phe Arg Met Leu Ser Pro Glu His Ala Pro Ala Glu
                885                 890                 895

Met Tyr Asp Ile Met Lys Thr Cys Trp Asp Ala Asp Pro Leu Lys Arg
            900                 905                 910

Pro Thr Phe Lys Gln Ile Val Gln Leu Ile Glu Lys Gln Ile Ser Glu
        915                 920                 925

Ser Thr Asn His Ile Tyr Ser Asn Leu Ala Asn Cys Ser Pro Asn Arg
    930                 935                 940

Gln Lys Pro Val Val Asp His Ser Val Arg Ile Asn Ser Val Gly Ser
945                 950                 955                 960

Thr Ala Ser Ser Ser Gln Pro Leu Leu Val His Asp Asp Val
                965                 970
```